United States Patent
Neethirajan et al.

(10) Patent No.: US 8,454,819 B2
(45) Date of Patent: Jun. 4, 2013

(54) POLY(ANILINE BORONIC ACID) POLYMERS AND METHODS OF USE

(75) Inventors: Sureshraja Neethirajan, Knoxville, TN (US); Michael S. Freund, Winnipeg (CA); Digvir J. Jayas, Winnipeg (CA)

(73) Assignee: University of Manitoba, Winnipeg, Manitoba (CA)

( * ) Notice: Subject to any disclaimer, the term of this patent is extended or adjusted under 35 U.S.C. 154(b) by 317 days.

(21) Appl. No.: 12/873,835

(22) Filed: Sep. 1, 2010

(65) Prior Publication Data
US 2011/0056846 A1    Mar. 10, 2011

Related U.S. Application Data

(63) Continuation-in-part of application No. PCT/CA2009/001679, filed on Nov. 25, 2009.

(60) Provisional application No. 61/238,914, filed on Sep. 1, 2009, provisional application No. 61/117,841, filed on Nov. 25, 2008.

(51) Int. Cl.
*G01N 27/26*    (2006.01)

(52) U.S. Cl.
USPC .............. 205/775; 204/415; 204/431; 528/6; 528/398; 528/394; 205/778.5; 422/82.02

(58) Field of Classification Search
USPC .............. 204/418, 431; 205/775; 528/6, 398; 528/394; 422/82.02
See application file for complete search history.

(56) References Cited

U.S. PATENT DOCUMENTS

| 6,003,362 | A | 12/1999 | Dieckmann et al. |
| 6,797,152 | B2 | 9/2004 | Freund et al. |
| 7,144,553 | B2 | 12/2006 | Lewis et al. |
| 2002/0029979 | A1* | 3/2002 | Freund et al. ................. 205/775 |
| 2002/0142477 | A1 | 10/2002 | Lewis et al. |
| 2002/0197390 | A1 | 12/2002 | Lewis et al. |
| 2003/0055212 | A1* | 3/2003 | Freund et al. ................. 528/422 |
| 2007/0093644 | A1 | 4/2007 | Deore et al. |
| 2009/0214762 | A1 | 8/2009 | Lewis et al. |

FOREIGN PATENT DOCUMENTS

| WO | WO 2005/054338 A1 | 6/2005 |
| WO | WO 2010/060195 A1 | 6/2010 |

OTHER PUBLICATIONS

Barsan et al., "Conduction model of metal oxide gas sensors," *Journal of Electroceramics*, 2001; 7(3): 143-67.

Capone et al., "Solid state gas sensors: state of the art and future activities," *Journal of Optoelectronics and Advanced Materials*, 2003; 5(5): 1335-48.

(Continued)

*Primary Examiner* — J. Christopher Ball
*Assistant Examiner* — Jennifer Dieterle
(74) *Attorney, Agent, or Firm* — Mueting Raasch & Gebhardt, P.A.

(57) ABSTRACT

The present invention includes sensors and systems that include a sensor. A sensor includes a sensor polymer, where the polymer includes a repeating unit having an anilineboronic acid-phosphate complex or an anilineboronic acid complexed with an alcohol or diol. The sensor polymer may be a copolymer, such as a random copolymer, a block copolymer, or an alternate copolymer. The present invention also provides methods for using the sensors described herein, including methods for detecting the presence of an analyte, such as $CO_2$, in a fluid.

34 Claims, 28 Drawing Sheets

OTHER PUBLICATIONS

Chen et al., "Ab initio and molecular mechanics (MM3) calculations on alkyl-and arylboronic acids," *J Phys. Org. Chem.*, Jun. 1998; 11(6): 378-386.

Chidsey et al., "Redox capacity and direct current electron conductivity in electroactive materials," *J Phys. Chem.*, Mar. 1986; 90(7): 1479-1484.

Colin et al., "Modification of a piezo-optical gas dosimeter system towards continuous gas sensing: a feasibility study with carbon dioxide," *Sensors and Actuators B: Chemical*, 2003; 90(1-3): 216-21.

Colthup et al., *Introduction to Infrared and Raman Spectroscopy*, New York, 1975. Academic Press: New York. Title Page, and Table of Contents.

Cooper et al., "Selective fluorescence detection of fluoride using boronic acids," *Chem. Commun.*, 1998; 13: 1365-1366.

Cui et al., "Potentiometric $pCO_2$ sensors using polyaniline-coated pH-sensitive electrodes," *Analyst*, 1998; 123; 1855-9.

Deore et al., "A Switchable Self-Doped Polyaniline: Interconversion between Self-Doped and Non-Self-Doped Forms," Jan. 14 2004; *J. Am. Chem. Soc.*, 126(1): 52-53. Available online Dec. 10, 2003.

Deore et al., "Conducting Poly(anilineboronic acid) Nanostructures: Controlled Synthesis and Characterization," *Macromol. Chem. Phys.*, Jun. 2008; 209(11): 1094-1105.

Deore et al., "Electroactivity of electrochemically synthesized Poly(Analine Boronic Acid) as a function of pH: role of self doping," *Chemistry of Materials*, Apr. 20, 2004; 16: 1427-32.

Deore et al., "Highly Cross-Linked, Self-Doped Polyaniline Exhibiting Unprecedented Hardness," *Chem. Mater.*, 2005; 17(15): 3803-3805.

Deore et al., "pH dependent equilibria of poly(anilineboronic acid)-saccharide complexation in thin films," *Macromolecular Chemistry and Physics*, Apr. 3, 2006; 207: 660-4.

Deore et al., "*Saccharide* imprinting of poly(aniline boronic acid) in the presence of fluoride," *Analyst*, Jun. 2003; 128(6): 803-806.

Deore et al., "Self-Doped Polyaniline Nanoparticle Dispersions Based on Boronic Acid—Phosphate Complexion," *Macromolecules*, Jan. 1, 2009; 42: 164-8.

Domaille et al., "Triphenylborane methanolysis and equilibrium association between triphenylborane or diphenylborinate esters and alcohols," *J Org. Chem.*, Jan. 1985; 50(2): 189-194.

English et al., "Biogenic amine vapor detection using poly(anilineboronic acid) films," *Sensors and Actuators B: Chemical*, Jun. 26, 2006; 115(2): 666-71.

Fabre et al., "Poly(aniline boronic acid)-based conductimetric sensor of dopamine," *Chemical Communications*, Dec. 12, 2003; 24: 2982-3.

Fernando et al., "Identification and use of potential bacterial organic antifungal volatiles in biocontrol," *Soil Biology and Biochemistry*, 2005; 37(5): 955-64.

Greenspan, "Humidity Fixed Points of Binary Saturated Aqueous Solutions," *Journal of Research of the National Bureau of Standards—A, Physics and Chemistry*, Jan.-Feb. 1977; 81A(1): 89-96.

Haeusler et al., "A novel thick film conductive type $CO_2$ sensor," *Sensors and Actuators B: Chemical*, Aug. 1996; 34(1-3): 388-95.

Herber et al., "A miniaturized carbon dioxide gas sensor based on sensing of pH-sensitive hydrogel swelling with a pressure sensor," *Biomedical Microdevices*, Sep. 2005; 7(3): 197-204.

Hooker et al., "Nanotechnology Advantages Applied to Gas Sensor Development," *The Nanoparticles 2002 Conference Proceedings*, Norwalk, Connecticut, 2002. Business Communications Company Inc. pp. 1-7.

Hu et al., "PEO-PPO-PEO triblock copolymer/Nafion blend as membrane material for intermediate temperature DMFCs," *Journal of Applied Electrochemistry*. 2008; 38(4): 543-550.

Huang et al., "Polyaniline, a novel conducting polymer. Morphology and chemistry of its oxidation and reduction in aqueous electrolytes," *J Chem. Soc. Faraday Trans. 1: Physical Chemistry in Condensed Phases*, 1986; 82: 2385.

Ileliji et al., "Detection of a developing hot spot in stored corn with a $CO_2$ sensor," *Applied Engineering in Agriculture*, 2006; 22(2): 275-89.

Jasinski et al., "Electrocatalytic gas sensors based on Nasicon and Lisicon," *Materials Science-Poland*, 2006; 24(1): 261-7.

Jensen et al., "Response time characteristics of the $pCO_2$ electrode," *Analytical Chemistry*, 1979; 51(12): 1972-7.

Kaneyasu et al., "A carbon dioxide gas sensor based on solid electrolyte for air quality control," *Sensors and Actuators B: Chemical*, Jul. 2000; 66(1-3): 56-58.

Kang et al., "Polyaniline: A polymer with many interesting intrinsic redox states" *Prog. Polym. Sci.*, 1998; 23(2): 277-324.

Kim et al., "Borate-nucleotide complex formation depends on charge and phosphorylation state," *J Mass. Spectrom.*, Jul. 2004; 39(7): 743-51.

Kim et al., "$CO_2$-sensing characteristics of $SnO_2$ thick film by coating lanthanum oxide," *Sensors and Actuators B: Chemical*, Jan. 2000; 62(1): 61-6. Available online Jan. 10, 2000.

Kim et al., "Esterification of borate with NAD+ and NADH as studied by electrospray ionization mass spectrometry and 11B NMR spectroscopy," *J. Mass. Spectrom.*, Jun. 2003; 38(6): 632-40.

Kinkade, "Bringing Nondispersive IR Spectroscopic Gas Sensors to the Mass Market," *Sensors Magazine*, Oct. 2000; 9: 83, 11 pgs.

Lee et al., "Carbon dioxide sensor using NASICON prepared by the sol-gel method," *Sensors and Actuators B: Chemical*, Apr. 1995; 25(1-3): 607-9.

Li et al., "Effect of thermal excitation on intermolecular charge transfer efficiency in conducting polyaniline," *Applied Physics Letters*, 2004; 85(7): 1187-9.

Lukachova et al., "Electroactivity of chemically synthesized polyaniline in neutral and alkaline aqueous solutions: Role of self-doping and external doping," *J. Electroanal. Chem.*, Mar. 13, 2003; 554: 59-63.

Luo et al., "Stable Aqueous Dispersion of Conducting Polyaniline with High Electrical Conductivity," *Macromolecules*, 2007; 40(23): 8132-8135.

Madrid et al., "Insects in stored cereals and their association with farming practices in southern Manitoba," *The Canadian Entomologist*, 1990; 122(5-6): 515-23.

Magan et al., "Volatiles as an indicator of fungal activity and differentiation between species, and the potential use of electronic nose technology for early detection of grain spoilage," *Journal of Stored Products Research*, 2000; 36(4): 319-40.

Mahmoudi et al., "Photoluminescence response of gas sensor based on $CH_x$/porous silicon—Effect of annealing treatment," *Materials Science and Engineering B*, 2007; 138(1-3): 293-7.

Maier et al., "Monitoring carbon dioxide levels for early detection of spoilage and pests in stored grain," *Proceedings of the 9th International Working Conference on Stored Product Protection*, Oct. 15-18, 2006. pp. 1174-1181.

Mandayo et al., "$BaTiO_3$-CuO sputtered thin film for carbon dioxide detection," *Sensors and Actuators B: Chemical*, 2006; 118(1-2): 305-310.

Moseley., "Solid state gas sensors," *Measurement Science and Technology*, 1997; 8(3): 223-237.

Muir et al., "Carbon Dioxide as an Early Indicator of Stored Cereal and Oilseed Spoilage," *Transactions of the ASBE*, 1985; 28(5): 1673-5.

Müller et al., "Fluorescence optical sensor for low concentrations of dissolved carbon dioxide," *Analyst*, 1996; 121(3): 339-43.

Mulrooney et al., "Detection of carbon dioxide emissions from a diesel engine using a mid-infrared optical fibre based sensor," *Sensors and Actuators A*, 2006; 136(1): 104-110.

Nakamura et al., "An optical sensor for $CO_2$ using thymol blue and europium (III) complex composite film," *Sensors and Actuators B: Chemical*, 2003; 92: 98-101.

Neethirajan et al., "Carbon dioxide ($CO_2$) sensors for the agri-food industry—A Review." *Food and Bioprocess Technology*, 2009; (2)115-21.

Neethirajan, Sureshraja. "Development of a Carbon Dioxide ($CO_2$) Sensor for Agri-Food Industry". Thesis Submitted to the University of Manitoba. Aug. 2009. 105 pages total.

Neoh et al., "Structural study of polyaniline films in reprotonation/deprotonation cycles," *J. Phys. Chem.*, Nov. 1991; 95(24): 10151-10156.

Nicolas et al., "New Boronic-Acid- and Boronate-Substituted Aromatic Compounds as Precursors of Fluoride-Responsive Conjugated Polymer Films," *Eur. J Org. Chem.*, May 2000; 2000(9): 1703-1710.

Parvatikar et al., "Electrical and humidity sensing properties of polyaniline/$WO_3$ composites," *Sensors and Actuators B: Chemical*, Apr. 26, 2006; 114(2): 599-603.

Pasierb et al., "Long-term stability of potentiometric $CO_2$ sensors based on Nasicon as a solid electrolyte" *Sensors and Actuators B: Chemical*, 2004. 101(12):47-56.

Proke et al., "Polyaniline prepared in the presence of various acids:2. Thermal stability of conductivity," *Polymer Degredation and Stability*, Oct. 2004; 86(1): 187-95.

Recksiedler et al., "Substitution and condensation reactions with poly(anilineboronic acid): reactivity and characterization of thin films," *Langmuir*, Apr. 12, 2005; 21(8): 3670-4.

Rego et al., "Carbon dioxide/methane gas sensor based on the peunselectivity of polymeric membranes for biogas monitoring," *Sensors and Actuators B: Chemical*, Sep. 29, 2004; 103(1-2): 2-6.

Segawa et al., "Sensitivity of fiber-optic carbon dioxide sensors utilizing indicator dye," *Sensors and Actuators B: Chemical*, Oct. 1, 2003; 94(3): 276-81.

Shimizu et al., "Solid electrolyte $CO_2$ sensor using NASICON and Perovskite type oxide electrode," *Sensors and Actuators B: Chemical*, Jun. 2000; 64(13):102-106.

Shoji et al., "Potentiometric Saccharide Detection Based on the $pK_a$ Changes of Poly(aniline boronic acid)," Journal of the American Chemical Society, 2002; 124: 12486-12493.

Sipior et al., "Phase Fluorometric Optical Carbon Dioxide Gas Sensor for Fermentation Off-Gas Monitoring," *Biotechnology Progress*, 1996; 12(2): 266-71.

Smith et al., "Nanotechnology Enabled Sensors: Possibilities, Realities, and Applications," *Sensors Magazine Online*, Nov. 1, 2003. Retrieved from the Internet May 19, 2011. <URL: http://www.sensorsmag.com/sensors/chemical-gas/nanotechnology-enabled-sensors-possibilities-realities-and-a-1074?print=1>, 4 pgs.

Socrates, *Infrared Characteristic Group Frequencies, 2nd edition*, New York, 1994. Title Page, Table of Contents, 5 pgs.

Stafström et al., "Polaron lattice in highly conducting polyaniline: Theoretical and optical studies," *Phys. Rev. Lett.*, Sep. 28, 1987; 59(13): 1464-1467.

Suzuki et al., "An integrated module for sensing $pO_2$, $pCO_2$, and pH," *Analytica Chimica Acta*, 2000; 405(1-2): 57-65.

Takeda, "A new type of $CO_2$ sensor built up with plasma polymerized poly aniline thin films," *Thin Solid Films*, 1999; 343-344, 313-36.

Tan et al., "Freeze damage detection in oranges using gas sensors," *Postharvest Biology and Technology*, 2005; 35:177-182.

Tongol et al., "Surface and electrochemical studies of a carbon dioxide probe based on conducting polypyrrole," *Sensors and Actuators B: Chemical*, Aug. 1, 2003; 93(1-3): 187-196.

Virji et al., "Polyaniline Nanofiber Gas Sensors: Examination of Response Mechanisms," *NANO Letters*, 2004; 4(3):491-6.

Viswanathan et al., "Is Nafion® the Only Choice?" *Bulletin of the Catalysis Society of India*, 2007; 6: 50-66.

Von Bultzingslöwen et al., "Sol-gel based optical carbon dioxide sensor employing dual luminopore referencing for application in food packaging technology," *The Analyst*, 2002; 127(11): 1478-1483.

Waghuley et al., "Application of chemically synthesized conducting polymer-polypyrrole as a carbon dioxide gas sensor," *Sensors and Actuators B: Chemical*, Jan. 15, 2008;128(2): 366-73.

Wang et al., "A novel carbon dioxide gas sensor based on solid electrolyte," *Sensors and Actuators B*, 2003; 88: 292-9.

Ward et al., "Novel processing of NASICON and sodium carbonate/barium carbonate thin and thick films for a $CO_2$ microsensor," *Journal of Material Science*, 2003; 38: 4289-92.

Westmark et al., "Influence of eluent anions in boronate affinity chromatography," *J. Chromatogr. A*, 1994; 664: 123-8.

Williams et al., "Microstructure effects on the response of gas-sensitive resistors based on semiconducting oxides," *Sensors and Actuators B: Chemical*, Nov. 2000; 70(1-3): 214-21.

Wudl et al., "Poly(p-phenyleneamineimine): Synthesis and Comparison to Polyaniline," *J. Am. Chem. Soc.*, 1987; 109(12): 3677-3684.

Yang et al., "Development of a Nasicon-based amperometric carbon dioxide sensor," *Sensors and Actuators B: Chemical*, Jan. 25, 2000; 62(1): 30-34.

Zhang et al., "In situ study of the conductivity of the electrochemically deposited polyaniline film using a dual-disk microelectrode". 1997. *Journ. of Electroanalytical Chemistry*. 440(1-2):35-39.

Zhu et al., "Solid-electrolyte NASICON thick film $CO_2$ sensor prepared on small-volume ceramic tube substrate," *Materials Chemistry and Physics*, 2005; 91(2-3):338-342.

Irimia-Vladu et al., "Suitability of emeraldine base polyaniline-PVA composite film for carbon dioxide sensing," *Synthetic Metals*, 2006; 156: 1401-1407.

Ogura et al., "A $CO_2$ Sensing Composite Film Consisting of Base-Type Polyaniline and Poly(vinyl alcohol)," *Electrochemical and Solid-State Letters*, 1999; 2(9): 478-80.

Oho et al., "A $CO_2$ sensor operating under high humidity," *J. Electroanalytical Chemistry*, 2002; 522: 173-8.

* cited by examiner

Finger length (f) = 8.075mm
Finger height (h) = 27 μm
Interdigitated spacing (w) = 100 μm
Number of electrodes = 4+5 = 9
Total area = 1.962225 mm$^2$ (a)

(b)

POLY(ANILINE BORONIC ACID) POLYMERS AND METHODS OF USE

CROSS-REFERENCE TO RELATED APPLICATIONS

This application claims the benefit of U.S. Provisional Application Ser. No. 61/238,914, filed Sep. 1, 2009, and is a continuation-in-part of International Application PCT/CA2009/001679, filed Nov. 25, 2009, which claims the benefit of U.S. Provisional Application Ser. No. 61/117,841, filed Nov. 25, 2008, each of which is incorporated by reference herein.

BACKGROUND

Evolving agriculture and food system has entered into a consumer driven era with consumers demanding food safety, quality and convenience. Data collection can be helpful to analyze, design, develop, manage, control and characterize the biological and environmental processes in the agri-food industry. For example, sensors are used in the field for monitoring environmental parameters to help producers in conducting more efficient irrigation or pest control programs, on harvesting machinery for measuring yield per unit area, during storage for measurement of product temperature, for post-harvest grading and sorting of fruits and vegetables, and for online monitoring of process parameters during processing.

Sensors for the agri-food industry exhibit several differences compared to the traditional industrial sensors in terms of the measurement parameters as well as the environment. The users of agricultural sensors require inter-operable measurement framework and relative ease in the interpretation of sensor data. The agri-food processes are typically more variable due to biological nature (Neethirajan et al., 2009, *Food and Bioprocess Technology* 2(2): 115-121) thus sensors require the capability to handle this variability. Environment surrounding raw as well as processed agricultural materials is usually complex. Presence of multiple microorganisms and other biological agents further makes the sensing of parameters in agri-food industry very challenging.

Plant gas exchange, atmospheric gas monitoring, soil carbon dioxide ($CO_2$) flux, biogas composition monitoring (Rego and Mendes, 2004, *Sensors and Actuators B* 103: 2-6; Reich, 1945, *Food Industries* 17(11):93-95) are areas in which monitoring $CO_2$ can be used. Monitoring of $CO_2$ with the help of sensors can be helpful in freeze damage detection in oranges (Tan et al., 2005, *Post Harvest Biology and Technology* 35: 177-182); in processing of alcohols and beverages (Marazuela et al., 1998, *Applied Spectroscopy* 51(10): 1257-1367), and in methanol and urea production.

Food packaging is often done under a modified atmosphere of nitrogen ($N_2$), $CO_2$, and oxygen ($O_2$), specific to a product and with a purpose to prevent microbial spoilage. Carbon dioxide is widely used in modified-atmosphere packaging and a decrease in its concentration is a sign of leakage in a package. Freshness and safety of modified atmosphere food packages can be determined by detection of $CO_2$ concentrations (Smolander et al., 1997, *Trends in Food Science and Technology* 8: 101-106; Jones, 1923, *Canadian Chemistry and Metallurgy* 7(7): 172-174). High $CO_2$ levels can affect quality of French fries during processing and therefore, monitoring of $CO_2$ levels can be used for controlling ventilation in potato storage facilities (Jayas et al., 2001, *Canadian Biosystems Engineering* 43(5): 5-12).

SUMMARY OF THE INVENTION

The present invention provides sensors. A sensor includes an electrode and a sensor polymer adjacent to the electrode. In some embodiments the sensor polymer includes a polymer having an anilineboronic acid-phosphate complex. The anilineboronic acid-phosphate complex may include a repeating unit having the formula

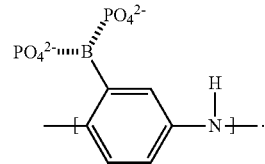

The polymer may be a copolymer, wherein the copolymer further includes a repeating unit having a formula selected from

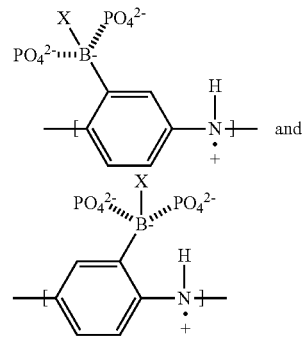

wherein X is fluoride or an amine. The copolymer may be a random copolymer, a block copolymer, or an alternate copolymer. An example of anilineboronic acid-phosphate complex present in the sensor polymer includes the formula

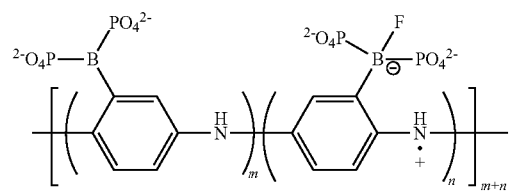

where m and n are each independently an integer greater than 2.

In some embodiments the sensor polymer includes a polymer having an anilineboronic acid complexed with an alcohol or diol. The anilineboronic acid complexed with an alcohol or diol may include a repeating unit having the formula

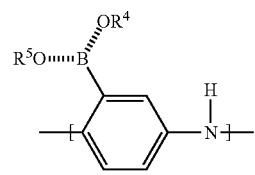

wherein $R^4$ and $R^5$ are each independently an organic group. The polymer may be a copolymer, wherein the copolymer further includes a repeating unit having a formula selected from

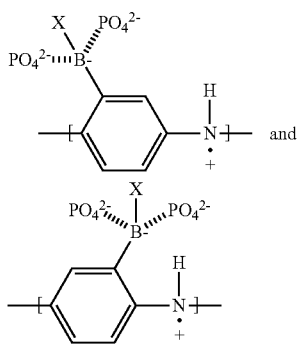

wherein X is fluoride or an amine. The copolymer is a random copolymer, a block copolymer, or an alternate copolymer.

The sensor may further include an electrolyte layer adjacent to the sensor polymer such that the sensor polymer is between the electrode and the electrolyte layer. The electrolyte layer may be electrically coupled to the sensor polymer. The electrolyte layer may include, for instance, water molecules, or a biological element, such as an enzyme. An electrolyte layer may be a hydrogel or a xerogel, and it may include a sulfonated tetrafluoroethylene based fluoropolymer-copolymer, a poly(vinyl alcohol), or an ionic liquid.

The sensor may further include a selective layer adjacent to the sensor polymer such that the sensor polymer is between the electrode and the selective layer, and it may further include an electrolyte layer adjacent to the sensor polymer such that the electrolyte layer is between the sensor polymer and the selective layer. The sensor may further include an analysis component electrically coupled to the electrode.

Also provided are systems for detecting an analyte in a fluid. A system may include a sensor that includes an electrode and a polymer adjacent to the electrode, wherein the sensor polymer will change an electrical characteristic in the presence of the analyte in the fluid, and an analysis component configured to detect a change in the electrical characteristic of the polymer. The polymer may be an anilineboronic acid-phosphate complex or an anilineboronic acid complexed with an alcohol or diol. The electrical characteristic may be resistance. The analyte may be $CO_2$, and an example of a selective layer is polytetrafluoroethylene. In some embodiments, a change in the electrical characteristic in response to $CO_2$ may be linear up to, for instance, 2750 parts per million (ppm) $CO_2$. The fluid may be a liquid or a gas. In some embodiments, the sensor may be present in a body of grain or other bulk-stored commodity.

The present invention also provides methods for detecting the presence of an analyte in a fluid. A method may include providing a sensor as described herein exposing the sensor to a fluid containing the analyte, and detecting a response to the exposure of the sensor to the analyte present in the fluid. The method may be used to detect an analyte, such as $CO_2$, in many environments, including, for instance, a body of grain or other bulk-stored commodity.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

In the following detailed description of the embodiments, reference is made to drawings which form a part hereof, and in which are shown by way of illustration specific embodiments that may be practiced. It is to be understood that other embodiments may be utilized and processing step/structural changes may be made without departing from the scope of the present disclosure. Alternative system embodiments may be identified herein by the use of a suffix, e.g., 100a, 100b, etc. It is understood that the description of a component (e.g., system 100, sensor 106, etc.) provided herein, where applicable and not otherwise indicated, applies to both components (e.g., both to the component without the suffix (system 100, sensor 106, etc.) and to the component with the suffix (system 100a, sensor 106a, etc.)).

Figure 1:
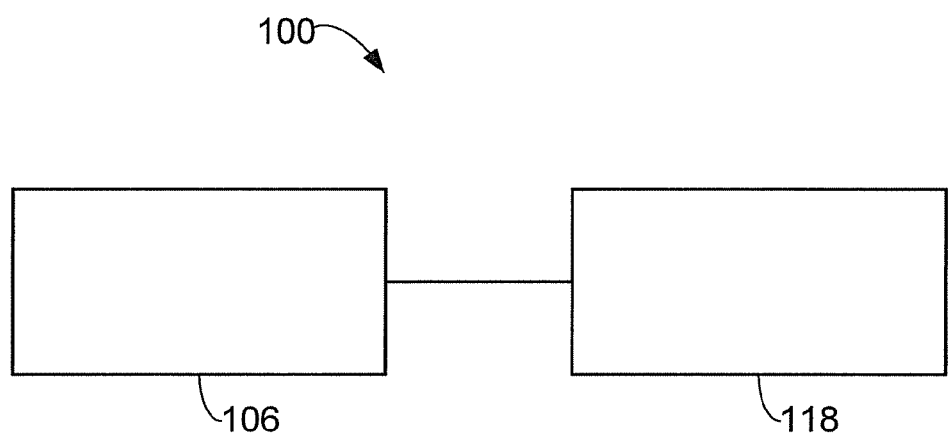
FIG. 1. Illustration of embodiments of a sensor system for detecting an analyte in a fluid.

FIG. 1 shows a general block diagram of an illustrative detection system 100 for use in detecting analyte in a fluid (e.g., liquid and gaseous solutions containing an amount of the analyte, and substantially pure liquid or gaseous samples of the analyte alone, or mixtures thereof). Generally, the system 100 includes one or more sensors 106 and optionally one or more analysis components 118.

At least one sensor 106 includes one or more components that respond to the presence of an analyte. Such a component may be, for instance, a polymer. For example, the response of a component of a sensor 106 is a change in an electrical characteristic such as electrochemical potential, conductivity, capacitance, impedance, or resistance.

One or more analysis components 118 are useable with one or more sensors 106 to provide sensor functionality. For example, one or more analysis components 118 may configured to receive and process response signals based on changes in an electrical characteristic of the one or more sensors 106. In various implementations, one or more analysis components 118 may be configured to receive and process such signals based on a variety of conventional measurements reflecting changes in an electrical characteristic of a sensor 106.

One or more analysis components 118 may be electrically coupled, and/or mechanically coupled, to one or more sensors 106. For example, one or more analysis components 118 may include appropriate signal-processing electronics and/or a programmable processor for processing the response signals. In some embodiments, one or more sensors may be coupled to a device, such as a general purpose computer system of conventional construction, that may include a programmable processor running a signal processing program (e.g., executing instructions) for identifying analytes and/or characteristics thereof based on the response signals received from sensor 106. In some embodiments, analysis component 118 may include circuitry (e.g., analog and/or digital hardware and/or software) configured to wirelessly transmit energy (e.g., through induction) and to wirelessly receive data signals.

One or more analysis components 118 may be configured to send a signal, by direct physical contact or wirelessly, to a control system. A control system may control a display to permit, for instance, observation of the electrical characteristic of the sensor 106, or provide control signal to any control components of a system, such as ventilators, switches, etc.

Figure 2:
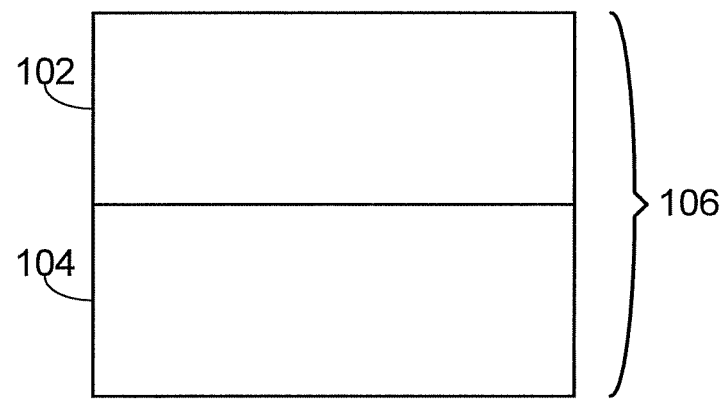
FIG. 2. Illustration of one embodiment of a sensor system.

In one exemplary embodiment illustrated in FIG. 2, a sensor 106 may include a sensor polymer 102 and an electrode layer 104. For example, the sensor polymer 102 and electrode layer 104 may be adjacent to each other, and electrically coupled.

The sensor polymer 102 may be formed from a polymer whose one or more electrical characteristics such as electrochemical potential, conductivity, capacitance, impedance, or resistance change upon changes to environmental conditions. For instance, in one embodiment a sensor polymer 102 is capable of undergoing a proton-coupled redox reaction. Polymers that are useful in the present invention are described in greater detail herein.

For example, an electrode layer 104 may include an anode and a cathode, or a source electrode and drain electrode. The electrode layer 104 may include any suitable electrodes. For instance, the electrodes may be micro-electrodes. For example, micro-electrodes may be arranged into an interdigitated array (IDA), i.e., at least a portion of an anode are placed substantially parallel to and in alternating succession with at least a portion of a cathode, e.g., in an alternating, finger-like pattern (see, for example, FIG. 15). The components of the electrode layer 104 may be made of any conductive material including, but not limited to, carbon, noble metals such as: gold, platinum, palladium, alloys of these metals, potential-forming (conductive) metal oxides and metal salts, as well as others.

Electrode layers 104 and their components can be of dimensions, meaning the width of the electrode components as well as the separation between components, that can provide an electrode layer with useful properties, e.g., useful or advantageous capabilities with respect to contacting a substance or measuring electrical properties. Advantageously, interdigitated arrays can be prepared at dimensions that allow for contact with and measurement of electrical properties of a relatively small sample of a substance, e.g., a polymer.

The dimensions of an electrode layer 104 are typically dependent upon the fabrication process used, such as microlithographic and nanolithographic processes, and the desired contact area between electrode layer 104 and sensor polymer 102. In some embodiments of the invention, each electrode element can independently have a width in the range from 15 micrometers to 50 micrometers, or a range from 20 micrometers to 40 micrometers. The separation between electrode components, especially the separation between alternating electrode elements, can be in the range between 20 micrometers and 150 micrometers, or a range from 75 micrometers to 125 micrometers. The length of each electrode element, i.e., each finger, can preferably be in the range from 2 millimeters (mm) to 15 mm, or a range from 5 mm to 10 mm. The total area of an electrode element (meaning the area of the fingers) can be chosen depending on these dimensions, on the use intended for the electrode, on the desired current level intended to pass through the electrode, and on the desired number of electrode elements. An exemplary area of an electrode having 9 electrode elements can be in the range from 0.2 to 5 square millimeters ($mm^2$), or a range from 0.5 $mm^2$ to 5 $mm^2$. The thickness of the electrode components can be sufficient to support a desired electric current. Smaller and larger electrodes are also possible.

Figure 3A:
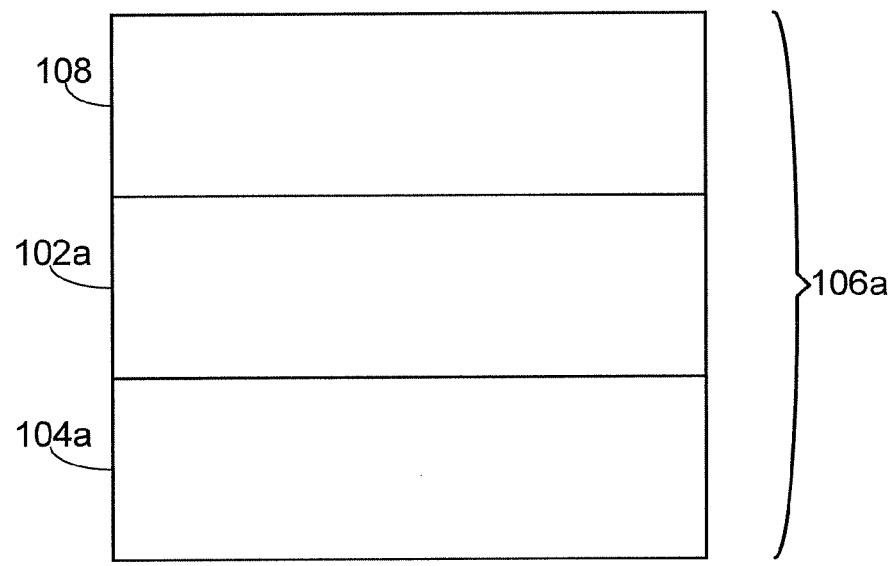
FIG. 3. Illustration of embodiments of a sensor system.

The sensor 106 may include additional elements. As shown in FIG. 3a, one exemplary embodiment of a sensor 106 may include one or more layers 108. Examples of layers 108 include an electrolyte layer. When present, an electrolyte layer may be adjacent to the sensor polymer 102. In some embodiments an electrolyte layer may be mechanically coupled (for example, may be in direct contact with a sensor polymer, or adjacent to but not necessarily in direct contact with a sensor polymer), electrically coupled, or both mechanically and electrically coupled to a sensor polymer 102.

An electrolyte layer may be configured to react with an analyte. For instance, an electrolyte layer may be the chemical that reacts with an analyte, or an electrolyte layer may include a chemical, that reacts with an analyte. The reaction between chemical and analyte may result in a product that can change the electrical characteristics of the adjacent sensor polymer 102. An example of such a product is a proton. Examples of chemicals include molecules such as water, and biological elements, such as an enzyme, substrate for an enzyme, or small molecule. For instance, in those embodiments where the chemical is an enzyme present in the electrolyte layer, reaction between the analyte and the enzyme may yield a proton which in turn protonates the sensor polymer 102. In those embodiments where the chemical is water present in the electrolyte layer, reaction between the analyte and water may yield a proton which in turn protonates the sensor polymer 102. More than one electrolyte layer may be present.

An electrolyte layer may be hydrophilic and optionally hygroscopic. A chemical may be attached to an electrolyte layer by, for instance, functionalization of the electrolyte layer surface. In embodiments where the electrolyte layer is a three dimensional lattice, a chemical may be chemically or physically entrapped. Examples of materials useful as an electrolyte layer include, but are not limited to, hydrogels or xerogels such as poly(vinyl alcohol), polymers such as polyelectrolytes, and liquids such as ionic liquids and ionic solutions. Electrolyte layers may have the properties of an acid catalyst and/or an ion exchange resin, including, for instance, perfluorinated ion-exchange polymers such as the sulfonated tetrafluoroethylene based fluoropolymer-copolymer available under the trade name Nafion (DuPont, Wilmington, Del.).

Figure 3B:
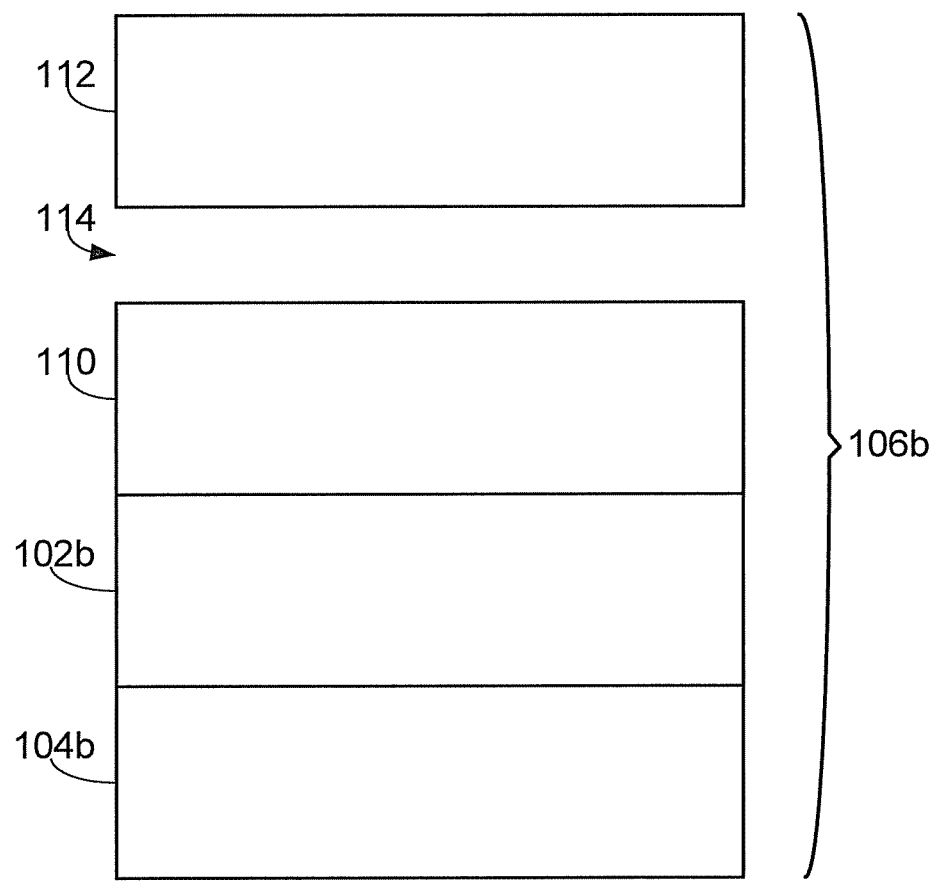
Figure 13:
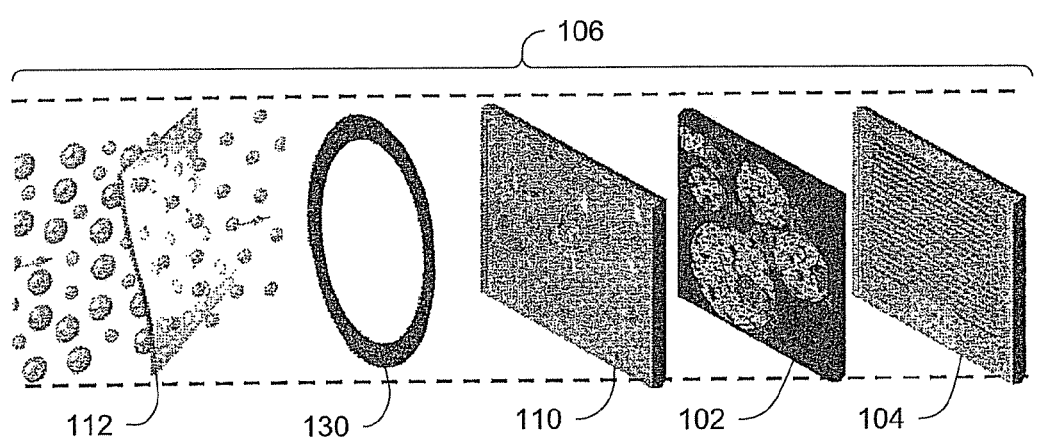
FIG. 13. One embodiment of an exemplary sensor system.

Another layer 108 that is an optional part of a sensor 106 is a selective layer. When present, a selective layer may be adjacent to the sensor polymer 102 or to the electrolyte layer if it is present. In some embodiments a selective layer may be mechanically coupled to the sensor polymer 102 or to the electrolyte layer if it is present. For example, a selective layer may be in direct contact with the sensor polymer 102 or to the electrolyte layer if it is present. Alternatively, the selective layer may be spaced away from the sensor polymer 102 or from the electrolyte layer if it is present. An example of such an embodiment is depicted in FIG. 3b, where the selective layer 112 may be spaced away from the electrolyte layer 110 to define a space 114 between the selective layer 112 and the electrolyte layer 110. Another example of such an embodiment is depicted in FIG. 13, where the selective layer 112 is spaced away from the electrolyte layer 110 by inclusion of a spacer 130, such as an O-ring, to define a space 114 between the selective layer 112 and the electrolyte layer 110. In some embodiments the space 114 may include a liquid, such as water.

A selective layer 112 may, for example, act to allow passage of the appropriate analyte or analytes, and limit passage of other molecules, from outside the sensor 106 to contact the electrolyte layer 110 and/or the sensor polymer 102. Not allowing other molecules to pass through may aid in reducing any cross-sensitivity effect of the sensor 106. In some embodiments a selective layer 112 may act to contain the electrolyte layer 110 when the electrolyte layer 110 is a liquid, such as an ionic solution or ionic liquid.

Selection of a suitable selective layer depends upon the analyte that is to traverse the width of a selective layer. Suitable selective layers include natural and synthetic polymers. In those embodiments where the sensor 106 is to detect $CO_2$, an example of a selective layer is polytetrafluoroethylene (PTFE), which is available under the trade name Teflon (DuPont, Wilmington, Del.). The thickness of a selective layer may depend upon the analyte or analytes to be detected. The average pore diameter of a selective membrane may depend upon the analyte or analytes to be detected and will include pores that permit passage of the analyte or analytes.

Figure 3C:
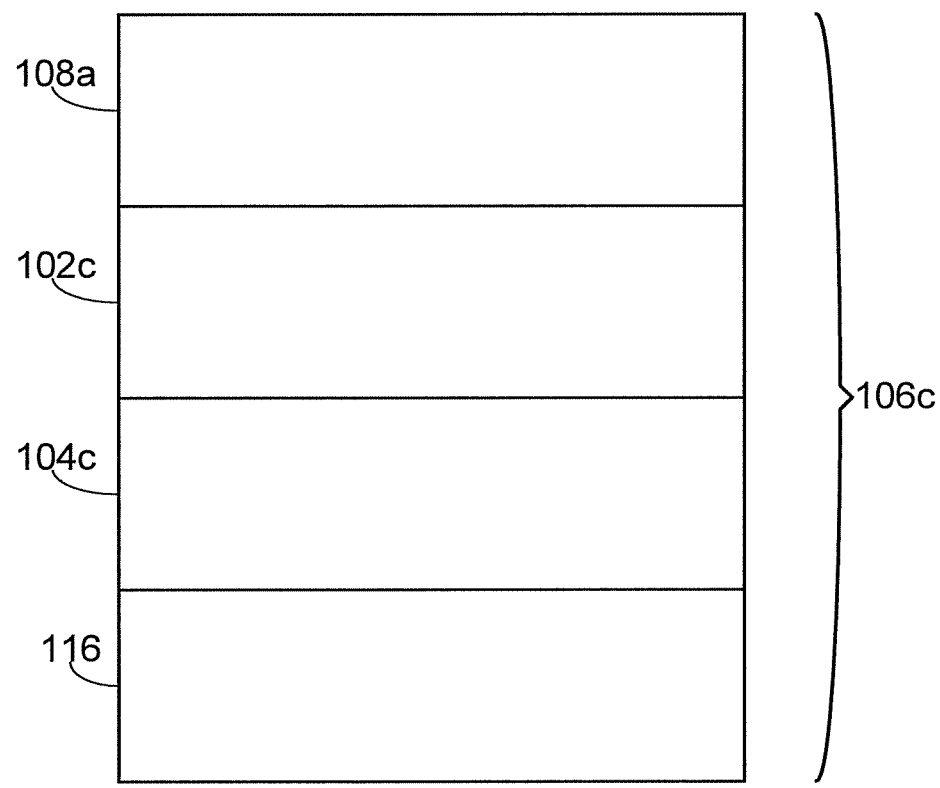

The sensor 106 may include a substrate 116, as shown in FIG. 3c, upon which an electrode layer 104, and/or other components of a sensor, may be placed. Suitable substrates are typically non-conductive and may act to mechanically support one or more sensor components. Examples of suitable substrates include, but are not limited to, silicon, ceramic, glass, aluminum oxide, and polyimide.

Figure 4:
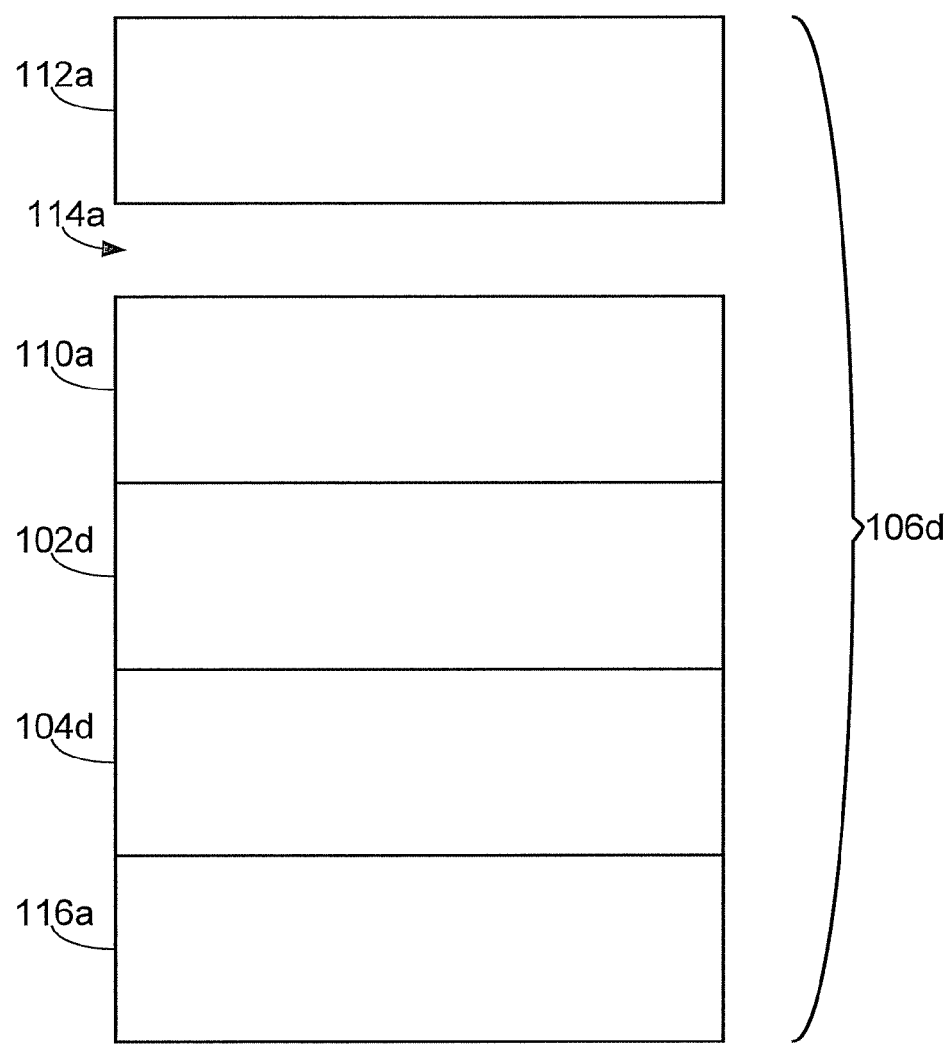
FIG. 4. Illustration of embodiments of a sensor system.

An exemplary embodiment of a system 100 is illustrated in FIG. 4. The sensor 106d of this exemplary system 100d includes a substrate 116a, an electrode layer 104d, a sensor polymer 102d, an electrolyte layer 110a, and a selective layer 112a separated from the electrolyte layer by a space 114a. In one example, such a sensor can detect $CO_2$. $CO_2$ present in the area around the sensor 106d can diffuse across the selective layer 112a, across the space 114a, and contact the electrolyte layer 110a. The CO2 may react with water present in the electrolyte layer 110a and optionally with water present in the sensor polymer 102d and forms a hydrogen ion H+. Without intending to be bound by theory, the hydrogen ion protonates the sensor polymer 102d and changes the resistance of the sensor polymer 102d. This change in resistance can be measured and processed by one or more analysis components.

Figure 14:
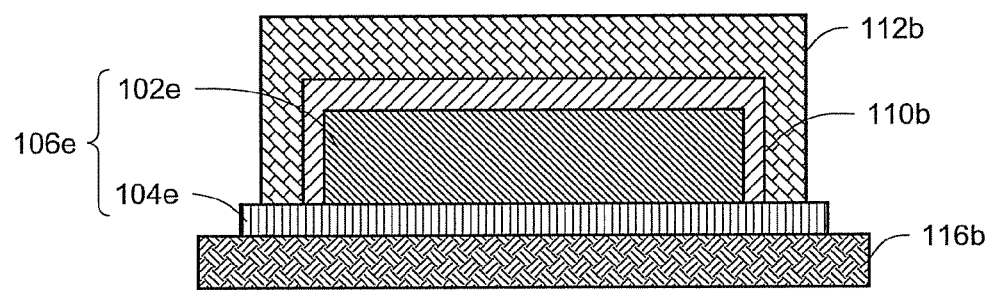
FIG. 14. Schematic side view of a constructed $CO_2$ sensor.

Another exemplary embodiment of a system 100 is illustrated in FIG. 14. The sensor 106e of this exemplary system includes a substrate 116b, an electrode layer 104e, a sensor polymer 102e, an electrolyte layer 110b, and a selective layer 112b. Analyte, for instance, $CO_2$ present in the area around the sensor 106e, can diffuse across the selective layer 112b and contact the electrolyte layer 110a. The $CO_2$ may react with water present in the electrolyte layer 110a and optionally with water present in the sensor polymer 102d and forms a hydrogen ion H+. The electrode layer 104e may include electrodes forming an interdigitated array such as, for instance, the type illustrated in FIG. 15.

Figure 5:
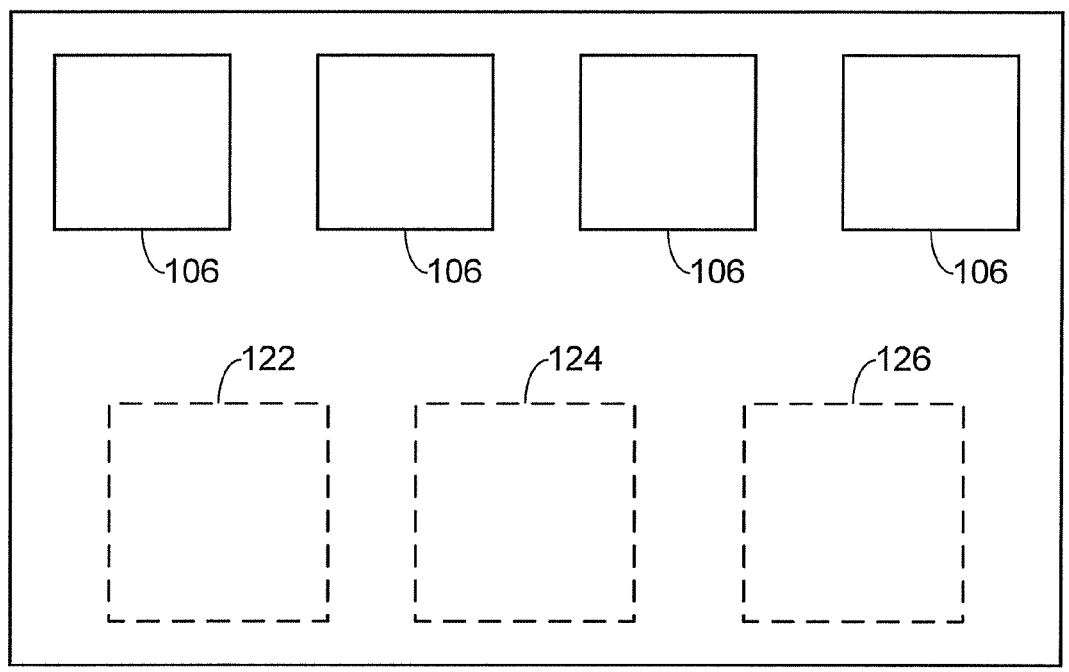
FIG. 5. Illustration of embodiments of a sensor array.

In some implementations a system 100 can include multiple sensors of similar or diverse construction, as in a sensor array. As shown in FIG. 5, such a sensor array may include one or more sensors 106, and optionally one or more other sensors, such as one or more humidity sensor 122, one or more temperature sensor 124, and/or one or more sensor 126 for an analyte other than the one to be detected by the sensor 106. The number of sensor 106 present in a sensor array can be a plurality, e.g., at least 1, at least 5, etc. In an embodiment shown in FIG. 16, an array may include sensors 106, connectors 128 that permit contact with an analysis component or with a connector located between a sensor and an analysis component, and one or more conductive connections between the electrodes of each sensor and the connectors. In one embodiment an analysis component may analyze signals from more than one sensor. For instance, an analysis component may include software for processing sample signals from multiple sensors and for analog to digital conversion of the signals.

Figure 34:
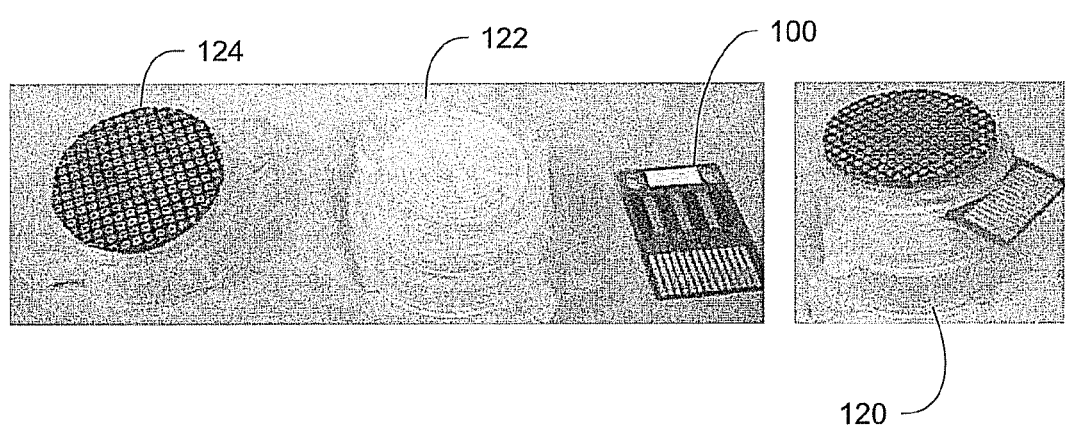
FIG. 34. Exploded and assembled view of a sensor assembly.

A sensor 106, such as a sensor 106 present in a sensor array, may be present in a sensor assembly 120. An exemplary embodiment of a sensor assembly 120 is illustrated in FIG. 34. A sensor assembly 120 generally provides for stably holding the sensor 106, for instance a sensor array, such as a sensor array illustrated in FIG. 16, in such a way that it is exposed to a fluid that includes the analyte to be sensed by the sensor 106, e.g., air or liquid around the sensor assembly. In addition to providing for stably holding the sensor, a sensor assembly may provide mechanical and/or chemical protection and prevent contamination of the sensor by undesirable components. A sensor assembly may also provide for connecting a sensor 106 to an analysis component 118.

A sensor assembly 120 may provide access to the environment by permitting the movement of the fluid through one surface of the sensor assembly 120, or the fluid may move through the sensor assembly, for instance, from one surface to another surface of the sensor assembly and across the sensor 106 such that an appropriate analyte in the fluid interacts with the sensor 106. Movement of the fluid may be by diffusion or forced by, for instance, a fan or a pump. Suitable structures will allow the fluid to pass and include, for instance, a mesh. A sensor assembly may include one or more parts, such as a sensor holder 122 and a cover 124. The characteristics of the fluid, the analyte to be detected, and the sensor 106 may influence the design of the sensor assembly.

The sensor polymer 102 is a self-doped polyaniline. In preferred embodiments, the self-doped polyaniline is a poly (anilineboronic acid) having moieties reacted with, bonded to, or complexed to the boronic acid group that provide negative charge to the boronic acid group, as further discussed herein below. Such moieties include, for example, phosphates, alcohols, and/or diols.

In some embodiments, the sensor polymer includes two or more repeating units including an anilineboronic acid-phosphate complex. The sensor polymer can be, for example, a homopolymer, or a copolymer including additional repeating units (e.g., aniline repeating units). An exemplary anilineboronic acid-phosphate complex repeating unit is illustrated as Formula I:

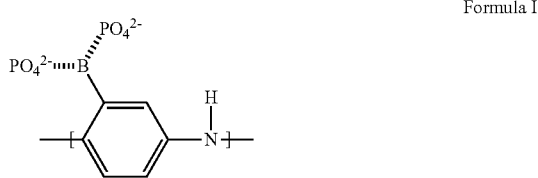

Formula I

The dashed line indicates that the phosphate ion ($PO_4^{3-}$) is complexed to the boron atom. In certain embodiments, at least one of the anilineboronic acid-phosphate complex repeating units further includes a nucleophilic species (e.g., fluoride ion and/or an amine) complexed or bonded thereto. Exemplary anilineboronic acid-phosphate complex repeating units further including a nucleophilic species (X) bonded thereto are illustrated as Formulas IIa and IIb:

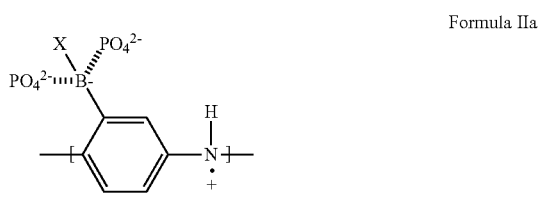

Formula IIa

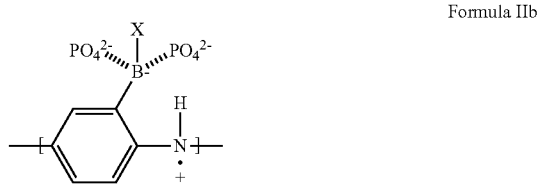

Formula IIb

The dashed line indicates that the phosphate ion ($PO_4^{3-}$) is complexed to the boron atom, and X represents a nucleophilic species such as fluoride ion or an amine, such as a primary amine or a secondary amine. For embodiments in which the polymer includes repeating units of Formula I and one or both of Formulas IIa and IIb (e.g., a copolymer), the ratio of number of repeating units of Formula I to the number of repeating units of Formulas IIa and IIb may be, for instance, between 3:1 and 3:3, such as 3:2. The copolymer can be, for example, a random copolymer, a block copolymer, or an alternate copolymer, and in preferred embodiments a random copolymer.

In other embodiments, the sensor polymer includes two or more repeating units including an anilineboronic acid complexed with an alcohol or diol. The sensor polymer can be, for example, a homopolymer, or a copolymer including additional repeating units (e.g., aniline repeating units). In certain embodiments, the anilineboronic acid complexed with an alcohol or diol may be represented as an anilineboronic acid ester. An exemplary anilineboronic acid ester is illustrated as Formula III:

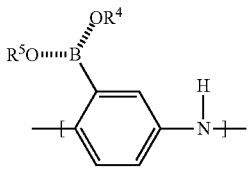

Formula III wherein $R^4$ and $R^5$ each independently represent an organic group (e.g., a C1-C12 organic group including aliphatic and/or aromatic groups). $R^4$ and $R^5$ can optionally be joined to form a ring. In certain embodiments, at least one of the anilineboronic acid ester repeating units further includes a nucleophilic species (e.g., fluoride ion and/or an amine) complexed or bonded thereto. Exemplary anilineboronic acid ester repeating units further including a nucleophilic species (X) bonded thereto are illustrated as Formulas IVa and IVb:

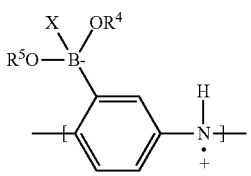

Formula IVa

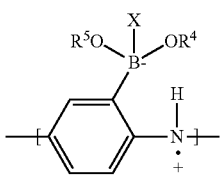

Formula IVb wherein $R^4$ and $R^5$ are defined as above, and X represents a nucleophilic species such as fluoride ion or an amine, such as a primary amine or a secondary amine. For embodiments in which the polymer includes repeating units of Formula III and one or both of Formulas IV and IVb (e.g., a copolymer), the ratio of number of repeating units of Formula III to the number of repeating units of Formulas IVa and IVb may be, for instance, between 3:1 and 3:3, such as 3:2. The copolymer can be, for example, a random copolymer, a block copolymer, or an alternate copolymer, and in preferred embodiments a random copolymer.

In certain embodiments, the sensor polymer 102 can be a self-doped polyaniline having the structure:

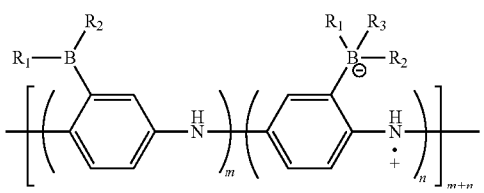

Formula V where m and n are each independently an integer greater than 2, and where $R^1$ and $R^2$ are each a moiety that binds to the boron to give it a negative charge. Examples of $R^1$ and $R^2$ include, for instance, phosphate ($PO_4^{3-}$), diols, and alcohols. $R^3$ may be, for instance, nucleophilic species, such as a fluoride, or an amine. The ratio of m to n in the polymer may be, for instance, between 3:1 and 3:3, such as 3:2.

A diol may be aromatic or aliphatic. In some embodiments the hydroxyl groups of a diol are adjacent (e.g., 1,1-gem diols or 1,2-vicinal diols), and in some embodiments (e.g., aromatic diols) the hydroxyl groups are co-planar. Examples of diols, include, but are not limited to, cis-1,2-cyclopentanediol, trans-1,2-cyclopentanediol, cis-1,2-cyclohexanediol, and trans-1,2-cyclohexanediol.

An alcohol may be aromatic or aliphatic. Examples include, but are not limited to, methanol, ethanol, and propanol.

An example of self-doped polyaniline useful as a sensor polymer is:

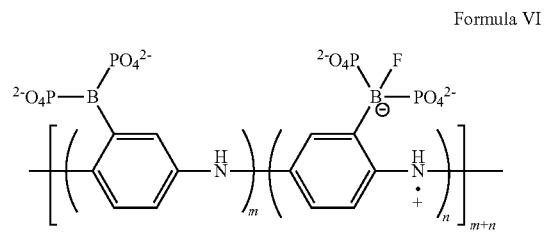

Formula VI where m and n are each independently an integer greater than 2.

A polymer may be produced by combining monomer, a nucleophilic species source, e.g., fluoride or amine source, a phosphate, diol, or alcohol source, and an oxidizing agent to form a mixture, and incubating under conditions suitable for polymerization. The monomer may be an aromatic boronic acid or a salt thereof. In general, the aromatic boronic acid may be, for example, a monomer that contains a boron that is anionic or can be converted into an anion (for example, sp3 form) through complexation with a moiety such as fluoride or an amine. For example the monomer may be boronic acid substituted aniline or a salt thereof, such as 3-aminophenyl boronic acid or a salt thereof, e.g., 3-aminophenylboronic acid hydrochloride salt.

Suitable sources of fluoride are those having a fluoride moiety. In general, the fluoride source may be a compound having a fluoride moiety that is available for complexing to a boron of the monomer having a boronic acid moiety. Examples include a soluble salt containing a fluoride moiety, such as a soluble salt containing a fluoride moiety that is capable of releasing free fluoride ($F^-$), e.g., a water soluble salt. For example, the fluoride source may be, but is not limited to, sodium fluoride, lithium fluoride or potassium fluoride.

Suitable sources of amine are those having an amine moiety. In general, the amine source may be a compound having an amine moiety that is available for complexing to a boron of the monomer having a boronic acid moiety. For example, the amine source may be, but is not limited to, substituted anilines and aliphatic anilines.

Suitable sources of phosphate are those having a phosphate moiety. In general, the phosphate source may be a compound having a phosphate that is available for interacting with boron of the monomer having a boronic acid moiety. Examples compounds having a phosphate moiety include an acid, a salt, an oligomer, a resin or a polymer having a phosphate moiety that is free to interact or complex with boron of the monomer having a boronic acid moiety. For example, a phosphate source may be, but is not limited to, sodium phosphate, potassium phosphate, rubidium phosphate, cesium phosphate, ammonium phosphate, poly(vinylphosphonic acid), or phosphoric acid.

Suitable oxidizing agents include an oxidizing agent capable of forming sufficient concentrations of an oxidized form of the polymer to permit polymerization. For example, an oxidizing agent may be, ammonium persulfate, ferric chloride, potassium dichromate, potassium permanganate, iodine, or a peroxide.

For instance, a polymer of the present invention may be produced by combining a monomer, such as 3-aminophenylboronic acid hydrochloride salt, at a concentration from 5 millimolar (mM) and 15 mM, a fluoride source, such as sodium fluoride, at a concentration from 40 mM to 60 mM, a phosphate source, such as phosphoric acid, at a concentration from 0.05 M to 1.5 M, and an oxidizing agent, such as ammonium persulfate, at a concentration of 1 mM to 10 mM. Conditions that are "suitable" for an event to occur, such as the production of a polymer, or "suitable" conditions are conditions that do not prevent such events from occurring. Thus, these conditions permit, enhance, facilitate, and/or are conducive to the event. Suitable conditions may include mixing the mixture, a temperature from 20° C. to 27° C., and incubation for 12 hours to 20 hours. The solvent may be water. The polymer may be isolated using standard methods, such as centrifugation. The polymer may also be purified by, for instance, using phosphoric acid.

The polymer may prepared by varying monomer to oxidant ratios from 1:025 to 1:2. Preferably, the monomer to oxidant ratios is 1:0.5. The polymer may be prepared under conditions to include a biological element such as an enzyme. Methods for including a biological element in a polymer are routine and include, for instance, mixing the biological element with the polymer, depositing the mixture of biological element and polymer, and allowing to dry.

The polymer may be in the fowl of a nanoparticle, and the nanoparticle may have a spherical shape or an irregular shape. For example, a nanoparticle may be from 1 nanometer (nm) to 100 nm, and any specific ranges or specific values within those ranges. For instance, a polymer of the present invention may be from 2 nm to 100 nm, 3 nm to 100 nm, 4 nm to 100 nm and so on to a range from 99 nm to 100 nm. Likewise, a polymer of the present invention may be from 1 nm to 99 nm, 1 nm to 98 nm, 1 nm to 97 nm and so on to a range from 1 nm to 2 m.

A polymer of the present invention has the property of changing conductivity at a pH range of between pH 5 and pH 10. A polymer of the present invention also has the property of forming dispersions in aqueous solutions, such as water. The ability of a polymer of the present invention to form a dispersion of nanoparticles is an advantage in that the polymer can be easily manipulated in processes for depositing polymers onto a surface.

In those embodiments where $CO_2$ is the analyte to be detected by a sensor 106, and the sensor 106 includes sensor polymer 102 of Formula I, an electrolyte layer and a selective layer, the system 100 typically displays a linear response to levels of $CO_2$ up to 2000 parts per million (ppm) $CO_2$, up to 2455 ppm, up to 2750 ppm, up to 3000 ppm, up to 3250 ppm, up to 3500 ppm, or up to 3750 ppm. Above that a saturation effect may be observed. Typically such a system 100 has a stable response to changes in analyte concentrations at various humidity levels up to a relative humidity (RH) of 65% RH, up to 70% RH, up to 75% RH, up to 80%, or up to 85% RH. Typically such a system 100 shows a saturated response to analyte between −25° C. to 45° C.

Systems and sensors described herein may be made using routine and well known methods. Methodologies building a system or a sensor are compatible with the MEMS process and can be mass manufactured using screen printing technology. The sensor polymer of the sensor may be deposited by electrophoretic methods, spraying, drop casting, or spin coating.

The present invention also provides methods for using the system 100. The methods generally include providing a system that includes at least one sensor 106, exposing the sensor to a fluid that may include an analyte that is to be detected, and measuring a response to the exposure of the sensor to the analyte. In some embodiments, the analyte is detected by virtue of its ability to change the degree of protonation of the polymer, e.g., increase protonation or decrease protonation. The sensor 106 may be present in essentially any location where an appropriate analyte may be, including, for instance, living and industrial systems. Exemplary embodiments include locations where the pH is in the range of pH 6 to pH 8. Examples of living systems include inside a body of an animal, such as a mouse, rat, chimpanzee, or other routinely used laboratory animal, or a human. The sensor may be located in a body cavity, in a location where it is exposed to blood or lymph, etc. Industrial systems include essentially any setting where the pH is generally in the range of pH 5 to pH 10. Without intending to be limiting, examples of industrial systems include locations where the sensor is exposed to a biological material, e.g., a test tube or other laboratory device for handling biological specimens. Other industrial systems include, but are not limited to, fermentation systems.

In some embodiments the sensor is in a location where relative humidity is no greater than 60%, not greater than 65%, no greater than 70%, or no greater than 75%. In some embodiments the sensor is in a location where the temperature is between −25° C. and 45° C.

In those embodiments where CO2 is the analyte to be detected, the sensor may be located in a living systems or in industrial systems such as agricultural and food industry applications, e.g., grain and fruit storage to permit monitoring of infestation and/or spoilage, fermentation devices, ventilation control, industrial incubator monitoring, food transportation, food processing, food quality monitoring and storage of horticulture commodities; bio-process industrial applications such as food freezing, dry-ice production, photo synthesis process, aquaculture, waste water treatment, beverage and carbonated drinks manufacturing, cold storage, cargo ships, in-situ fermentation processes in a bioreactor, food processing environment, and bioprocesses monitoring, and buildings for air quality measurement.

Also include in the present invention are methods for using the polymer described herein. In addition to the use of the polymers in the systems and sensors described herein, the polymer may be used in, for instance, formulations for coatings and inkjet printing.

The present invention is illustrated by the following examples. It is to be understood that the particular examples, materials, amounts, and procedures are to be interpreted broadly in accordance with the scope and spirit of the invention as set forth herein.

Example 1

Materials. 3-Aminophenylboronic acid hydrochloride salt (3-APBA) and ammonium persulfate were purchased from Aldrich Chemical Inc. Sodium fluoride, potassium chloride, sodium phosphate, and phosphoric acid (85%) were purchased from Fisher Scientific. Bulk distilled water was filtered then ion exchanged to yield 18.2 MΩ·cm quality water using Milli-Q-Academic A10 (Millipore Corp.). Indium-doped tin oxide-coated glass slides (ITO, 6±2 Ω/sq) were purchased from Delta Technologies Ltd. Gold interdigitated array microelectrodes (IDAs) were obtained from Biomedical Microsensors Laboratory at North Carolina State University. Each of these arrays contained 2.8 mm 0.075 mm gold electrodes with a gap width of 20 µm that had a total exposed area of 0.069 mm2. TEM Formvar-carbon coated copper grids (400 mesh) were purchased from CANEMCO-MARIVAC.

Synthesis of PABA/Phosphate Dispersions. PABA dispersions were synthesized using 10 mM (3-APBA) (monomer) and 50 mM sodium fluoride in 0.1 M phosphoric acid (20 mL) by adding 5 mM ammonium persulfate (oxidizing agent). Polymerization of 3-APBA was not observed in the absence of fluoride. A minimum of 1 mol equiv of fluoride to monomer was required to obtain conducting PABA with >50% yields. The mixture was stirred at room temperature, and the reaction was allowed to proceed for 16 h. In phosphoric acid, PABA was well suspended under the polymerization conditions. As a result, PABA was isolated via centrifugation and subsequently purified (to remove excess reactants and byproducts) using 0.1 M phosphoric acid. Finally, the polymer was redispersed in 0.1 M phosphoric acid without fluoride. The dispersion of PABA nanostructures prepared in 0.1 M phosphoric acid is stable indefinitely (no settling was observed over a 2 month period) with a maximum concentration of 5 mg/mL. PABA dispersions can be prepared in concentrations up to 20 mg/mL; however, they do not remain suspended indefinitely. The dispersion of nanostructures was coated on gold IDAs and ITO electrodes for electrochemical and spectroscopic characterization.

Characterization. The morphology of the PABA dispersion was examined by transmission electron microscopy (TEM, JEOL JEM-2000FX). TEM samples were prepared by diluting the purified product and casting the dispersion onto copper grids. UV-vis absorption spectra of PABA dispersions were obtained using an Agilent 8453 spectrophotometer. Fourier transform infrared (FTIR) spectra were obtained using a Nexus 870 spectrometer (Thermo Nicolet Corp.) equipped with an attenuated total reflectance (ATR) accessory. FTIR-ATR spectra of dry PABA powders were collected using a hemispherical germanium optical crystal and a deuterated triglycine sulfate and thermoelectrically cooled (DTGS TEC) detector (Clarke et al., 1998, Surface Analysis of Polymers by XPS and Static SIMS; Cambridge University Press: New York, p 44). Interferograms were accumulated to obtain each FTIRATR spectrum at a spectral resolution of 8 cm−1. Cyclic voltammetric and potential dependence drain current ($I_D$-$V_G$ characteristic) measurements were performed using a CH Instrument CHI 760 electrochemical workstation. For both measurements, a three-electrode configuration was used including a Pt wire counter electrode, Ag/AgCl as a reference electrode, and gold IDA as a working electrode. The potentials were scanned from negative to positive directions. $I_D$-$V_G$ characteristics were obtained by cycling the potential of the two adjacent PABA-coated microelectrodes (connected to W1 and W2 working electrode terminals of the bipotentiostat) maintaining a 50 mV potential difference between them. $^{11}$B NMR studies were carried out using a Bruker AMX 500 NMR spectrometer. The samples were prepared by adding 10% $D_2O$ in the monomer and polymer solution in 0.1 M phosphoric acid. Chemical shifts were determined relative to borontrifluoride etherate as a reference. X-ray photoelectron spectroscopic (XPS) analyses were carried out using Kratos Axis Ultra spectrometer with a base pressure of 2 10$^{-10}$ mbar (UHV). A monochromatized Al Kα radiation source (hv) 1486.70 eV) was used. The X-ray electron gun was operated at 15 kV and 20 mA. The kinetic energy of the photoelectrons was analyzed in a multichannel delay-line detector (DLD) (Briggs, 2003, Surface Analysis by Auger and X-ray Photoelectron Spectroscopy; IM Publication: Chichester, UK, p 138). Survey and high-resolution spectra were collected using 160 and 40 eV pass energies, respectively. The analyzed area of the samples was 700 300 µm2. Spectra were acquired with electron charge compensation in operation to avoid sample charging. The binding energy scale was referenced to the C 1s peak of PABA, which was set to 284.6 eV. Core peaks were analyzed using a nonlinear Shirley-type background, and peak positions and areas were obtained by weighted least-squares fitting of model curves (70% Gaussian, 30% Lorentzian) to the experimental data. On the basis of the best practice of fitting the data for PABA, the maximum values of the fwhm were assigned for every single element, which were maintained equal during the component fit. The positions of component peaks were optimized to give the best fit to the experimental spectrum. The surface elemental compositions were determined by the ratios of peak areas corrected with sensitivity provided by Kratos for the Axis Ultra analyzer (Clarke et al., 1998, Surface Analysis of Polymers by XPS and Static SIMS; Cambridge University Press: New York, p 44).

Results and Discussion

The polymerization of 3-APBA in the presence of fluoride and phosphoric acid results in a stable PABA dispersion. In our previous studies, PABA dispersions consisting of 2-15 nm particle sizes were obtained using 0.1 M HCl and fluoride; however, they only remained suspended for 1 day (Deore et al., 2008, Macromol. Chem. Phys., 209:1094). In contrast, the larger size PABA particle dispersions prepared in the presence of phosphoric acid and fluoride are stable indefinitely; no settling was observed over a 2 month period at a concentration of 5 mg/mL. These results suggest that the stability of the dispersions in phosphoric acid relative to hydrochloric acid is due to the interaction of the phosphate with the boronic acid substituent.

In order to explore this chemistry in more detail, an XPS study was performed on PABA film prepared from dispersions and rinsed with water. PABA dispersion was prepared in 0.1M phosphoric acid and fluoride, and then it was purified and redispersed in the 0.1 M phosphoric acid without fluoride. The percentages of neutral nitrogen, positively charged nitrogen, B:F and B:P ratios in the PABA film are shown in Table 1. The neutral nitrogen is the sum of the two lowest binding energy components within the N 1s envelope and are attributed to the quinoid imine (—N═), ~398.1 eV) and benzenoid amine (—NH—, ~399.5 eV). The doping level of the polymer can be determined quantitatively based on the amount of dopant and the positively charged nitrogen (N+, >400 eV) by deconvoluting the N 1s core-level spectrum (Neoh et al., 1991, J. Phys. Chem., 95:10151, Kang et al., 1998, Prog. Polym. Sci., 23:277). Generally, in externally doped PANI with HCl, $H_2SO_4$, etc., the percentages of dopant and positively charged nitrogen are approximately same (Neoh et al., 1991, J. Phys. Chem., 95:10151, Kang et al., 998, Prog. Polym. Sci., 23:277). In PABA, the percentage of fluoride dopant is approximately the same as the positively charged nitrogen; however, the percentage of phosphate is in excess (see Table 1). These results suggest that the PABA prepared in the presence of phosphoric acid and fluoride involves the complexation of boron to phosphate and fluoride. On the basis of the B:P ratio, all borons in polymer are bound to two phosphate groups. However, the fluoride is associated with ~40% of the total polymer.

TABLE 1

N 1s Composition and Boron to Dopant Ratios in PABA/Phosphate Film Prepared from Dispersion.

| | |
|---|---|
| % N | 71 |
| % N+ | 29 |
| B:N | 1:1 |
| B:F | 1:0.4 |
| B:P | 1:2 |

Figure 6:
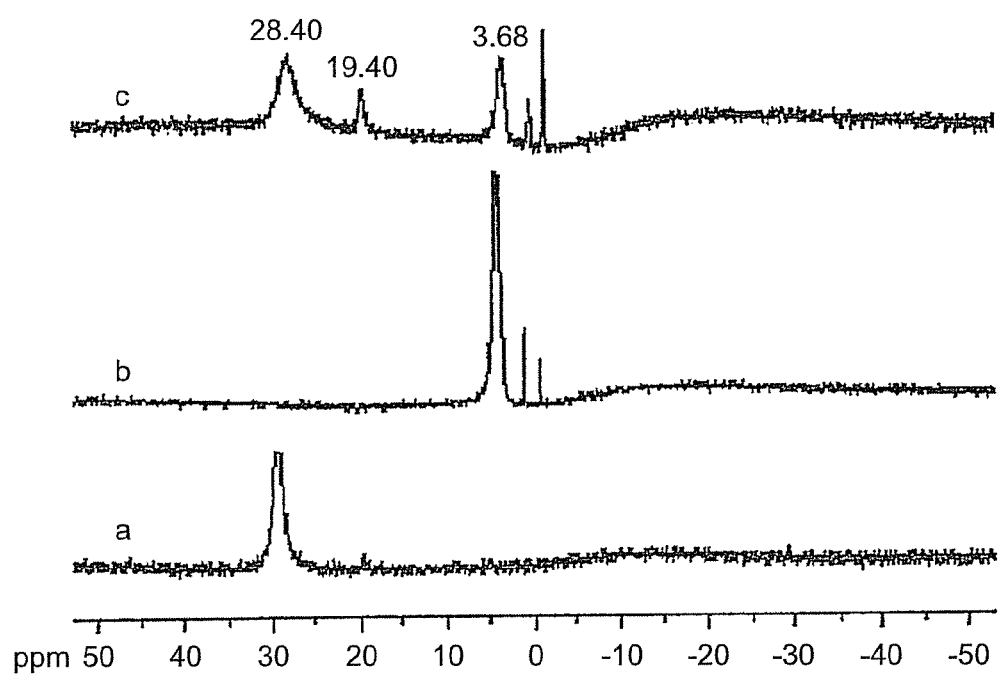
FIG. 6. $^{11}B$ NMR spectra of monomer solution (a) 10 mM 3-APBA in 0.1 M phosphoric acid, (b) 10 mM 3-APBA+50 mM NaF in 0.1 M phosphoric acid, and (c) polymer dispersion prepared using 10 mM 3-APBA+50 mM NaF+5 mM of ammonium persulfate in 0.1 M phosphoric acid and purified using 0.1 M phosphoric acid.
Figure 7:
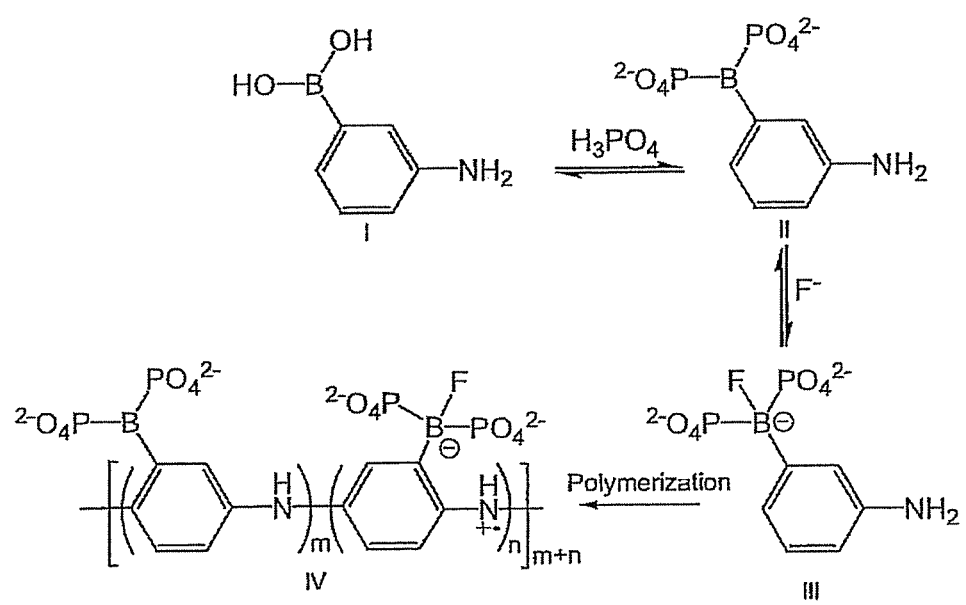
FIG. 7. Proposed Mechanism of 3-APBA-Phosphate Complexation and Polymerization.

The chemical structure of PABA was further studied with $^{11}$B NMR by examining of both monomer and polymer solutions in phosphoric acid as shown in FIG. 6 The chemical shift of the $^{11}$B NMR signal of boronic acids is dependent on the hybridization state of the boron atom (trigonal versus tetrahedral). The $^{11}$B NMR spectrum of the monomer in phosphoric acid (FIG. 6a) shows a single resonance with a chemical shift of 28.8 ppm, indicating that boron exists primarily in the neutral trigonal form (FIG. 7, II) (Domaille et al., 1985, *J. Org. Chem.,* 50:189). However, in the presence of sodium fluoride (FIG. 1b), a resonance signal is observed ~25 ppm upfield, indicative of the formation of tetrahedral anionic boronate (FIG. 7, III) (Westmark et al., 1994, *J. Chromatogr., A,* 664:123, Cooper et al., 1998, *Chem. Commun.,* 1365). Following the addition of an oxidizing agent, completion of the polymerization reaction, purification, and redispersion in 0.1M phosphoric acid without fluoride, the $^{11}$B NMR spectrum was taken again (FIG. 1c). The spectrum shows that the boron exists in both trigonal boronic acid and tetrahedral anionic boronate form (FIG. 7, IV). The amount of tetrahedral boronate is ~35%. These results suggest that in monomer solution fluoride stabilizes tetrahedral boron (FIG. 7, III), which in turn allows oxidation of the monomer. Once the polymer is formed and oxidized, the oxidized backbone stabilizes the boron-phosphate complexation. The existence of multiple peaks in the PABA nanoparticle dispersion suggests that there are both tetrahedral and trigonal forms of boron which do not interconvert on the NMR time scale (Kim et al., 2003, *J. Mass Spectrom.,* 38:632, Kim et al., 2004, *J. Mass Spectrom.,* 39:743) as indicated by the peaks at 3.68 and 28.40, respectively, as well as some fraction of boron groups which experience fast interconversion, resulting in an averaged peak position (Kim et al., 2003, *J. Mass Spectrom.,* 38:632, Kim et al., 2004, *J. Mass Spectrom.,* 39:743) of 19.40 ppm. The percentage of tetrahedral boronate is in agreement with the percentage of positively charged nitrogen obtained from XPS study and suggests that the PABA is self-doped in phosphoric acid in the presence of fluoride and self-stabilized likely due to the formation of boron-phosphate complex. On the basis of both XPS and $^{11}$B NMR results, the structure of self-doped PABA is composed of around 40% n and 60% m repeat units as shown in FIG. 2, IV. PABA/phosphate dispersions were prepared by varying monomer to oxidant ratios from 1:0.25 to 1:2. The stability of PABA particle dispersion with time as well as the redox conductivity as a function of pH was found to be higher at monomer to oxidant ratios of 1:0.5 due to the higher degree of self-doping at the optimum polymerization rate.

The PABA dispersion was purified and redispersed in the 0.1 M phosphoric acid without fluoride. The morphology of PABA prepared in 0.1 M phosphoric acid and fluoride was somewhat similar to that obtained in 0.1 M HCl and fluoride. In 0.1 M HCl solution and fluoride, spherical nanoparticles with diameter in the range of 2-15 nm are obtained (Deore et al., 2008, *Macromol. Chem. Phys.,* 209:1094). However, phosphate doped and complexed PABA produces irregular shape particles with size range 25-50 nm. The difference observed in the size and shape of PABA prepared in phosphoric acid can be attributed to the boron-phosphate complexation.

Figure 8:
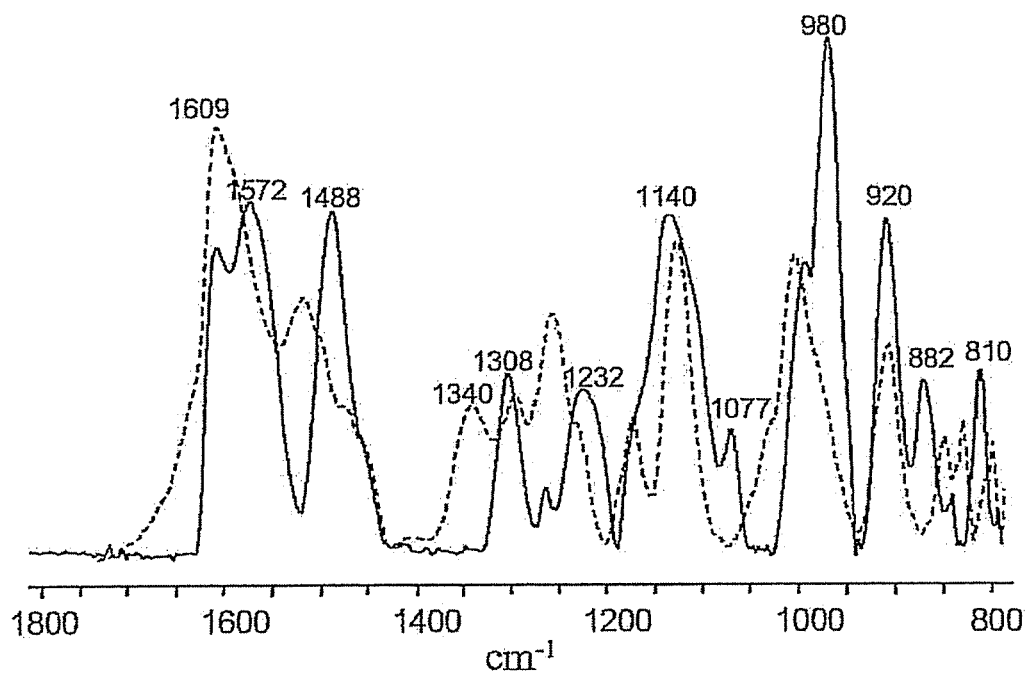
FIG. 8. FTIR-ATR spectrum of PABA/phosphate dried powder (solid line) and PABA prepared chemically using 0.5 M HCl in the presence of fluoride (dashed line).

The FTIR-ATR spectrum of PABA/phosphate nanostructures depicts all of the characteristic bands of PANI and boron-phosphate interactions as shown in FIG. 8, solid line. IR bands characteristic of PANT are observed at 1609, 1488, and 1140 cm$^{-1}$ corresponding to quinoid, benzenoid, and the aromatic C—N stretching ring modes (Epstein et al., 1991, In: *Spectroscopy of Advanced Materials*; John Wiley & Sons: New York). The characteristic bands of the B—F stretching modes are observed at 810, 850, and 882 cm$^{-1}$ (Socrates, 1994, *Infrared Characteristic Group Frequencies,* 2nd ed.; John Wiley & Sons: New York). However, the asymmetric B—O stretching mode generally observed at 1340 cm$^{-1}$ in boronic acids, as shown in FIG. 3, dashed line, is not present in PABA/phosphate. Bands characteristic of phosphate are observed at 920, 980, 1077, 1232, and 1308 cm$^{-1}$ (Socrates, 1994, *Infrared Characteristic Group Frequencies,* 2nd ed.; John Wiley & Sons: New York). The appearance of a sharp peak at 1572 cm$^{-1}$ is attributed to the B—N dative bond (Colthup et al., 1975, *Introduction to Infrared and Raman Spectroscopy*; Academic Press: New York, Chen et al., 1998, *J. Phys. Org. Chem.,* 11:378). However, this peak is not observed for PABA synthesized chemically without phosphate (FIG. 3, dashed line) (Deore et al., 2005, *Chem. Mater.* 17:3803, Recksiedler et al., 2005, *Langmuir,* 21:3670). Therefore, the presence of the peak at 1572 cm$^{-1}$ and the absence of B—O stretching mode further supports that the other interactions such as boron-phosphate likely contribute to this peak, as shown in FIG. 7, IV.

Figure 9:
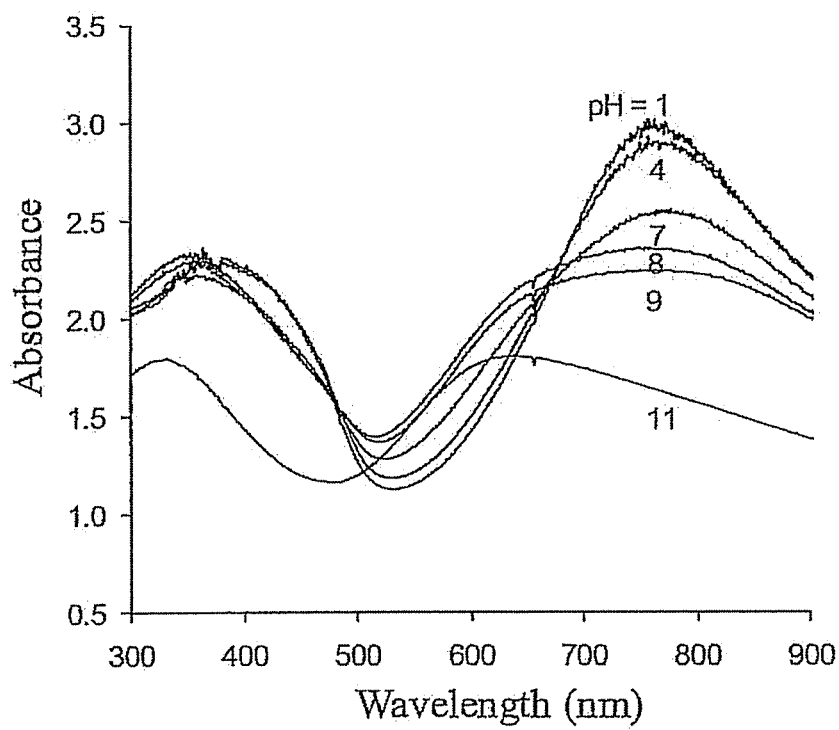
FIG. 9. UV-vis spectra of PABA/phosphate dispersion as a function of pH.
Figure 10:
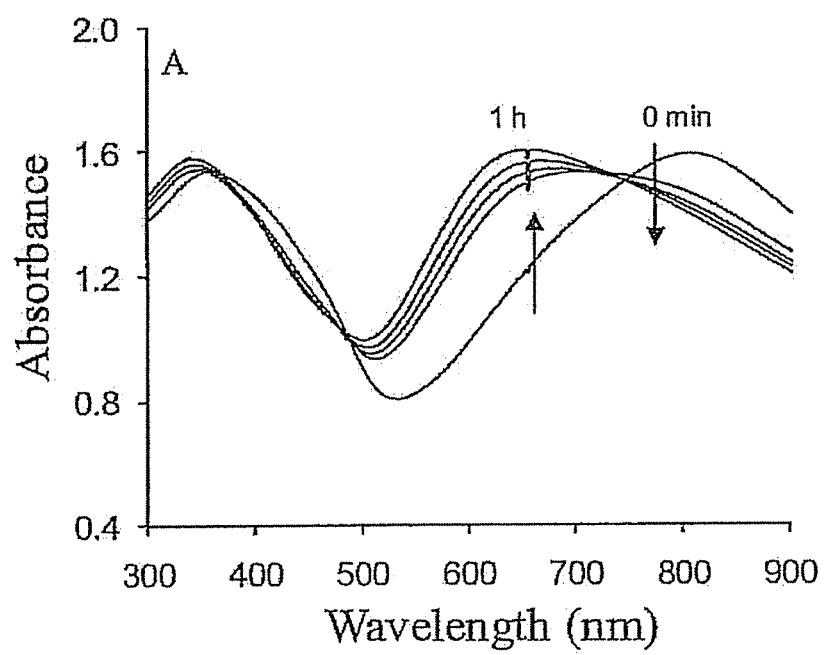
FIG. 10. UV-vis spectra of PABA/phosphate in (A) phosphate buffered saline (with NaCl) and (B) phosphate solution (without NaCl) at pH 7.4 as a function of time.
Figure 10:
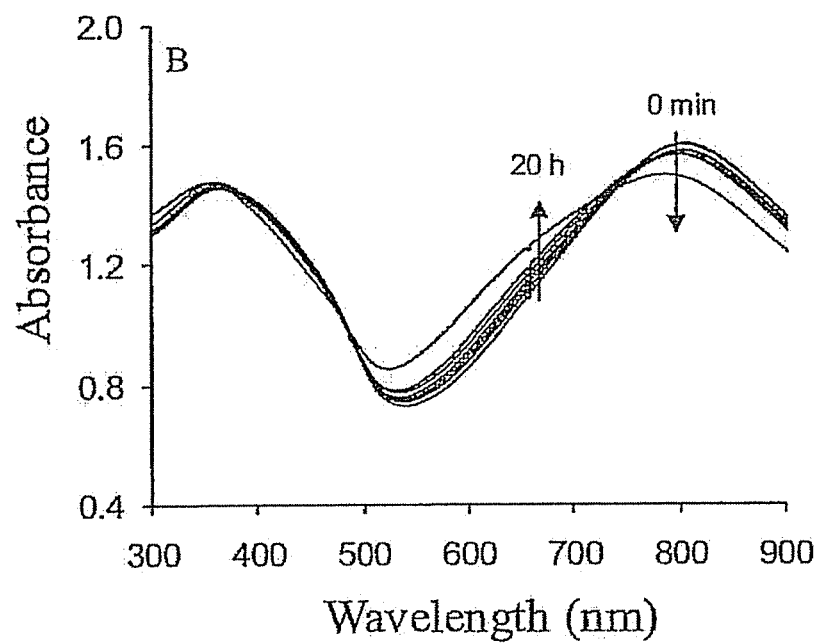

The above spectroscopic results confirm the boron-phosphate interaction and formation of self-doped PABA. To further explore the role of phosphate, optical, electrochemical, and in situ conductivity properties of PABA as a function of pH have been studied. FIG. 9 shows the UV-vis spectra of PABA dispersion as a function of pH. PABA dispersed in 0.1 M phosphoric acid resulted in a pH of 1, and the pH of the dispersion was subsequently increased by titrating with 1 M NaOH. The characteristic absorption bands around 320 and 800 nm assigned to π-π* and bipolaron band transitions, respectively, are observed up to pH 7 (Stafstrom et al., 1987, *Phys. Rev. Lett.,* 59:1464, Wudl et al., 1987, *J. Am. Chem. Soc.,* 109:3677). The existence of these bands in the PABA dispersion indicates that the polymer is in the conducting emeraldine salt state up to pH 7. At pH values 8 and 9, the bipolaron band remained at 700-800 nm; however, it broadens and exhibits a slight blue shift. At a pH value of 11, the presence of a broad peak at 620 nm suggests the complete dedoping of PABA to the emeraldine base form of the polymer. The PABA dispersion was stable and remained green up to pH 9. Above pH 9, the nanoparticles undergo a color change from green to blue, consistent with dedoping as well as flocculation. The flocculation of nanoparticles results in a decrease in absorbance at pH 11 due to scattering. The dedoping of polymer obtained upon exposure to alkaline pH is likely due to removal of phosphate and fluoride and conversion from emeraldine salt to the base form (Deore et al., 2004, *J. Am. Chem. Soc.,* 126:52). In order to verify these results, the stability of PABA dispersion in pH 7.4 phosphate buffer with and without NaCl was examined as a function of time (FIG. 10). The conversion of the dispersion from emeraldine salt to the base faun of PABA is observed at pH 7.4 in the presence of phosphate buffered saline (containing NaCl) solution as shown in FIG. 5A. In contrast, the PABA dispersion is highly stable in pH 7.4 phosphate buffered solution (in the absence of NaCl) as a function time (FIG. 5B). These results suggest that boron forms an anionic tetrahedral boronate group in the presence of phosphate and fluoride, resulting in self-doping, and imparts conductivity stability of PABA dispersion as a function of pH. The exchange of phosphate with other anions such as chloride or hydroxide results in the dedoping of the PABA dispersion.

Figure 11:
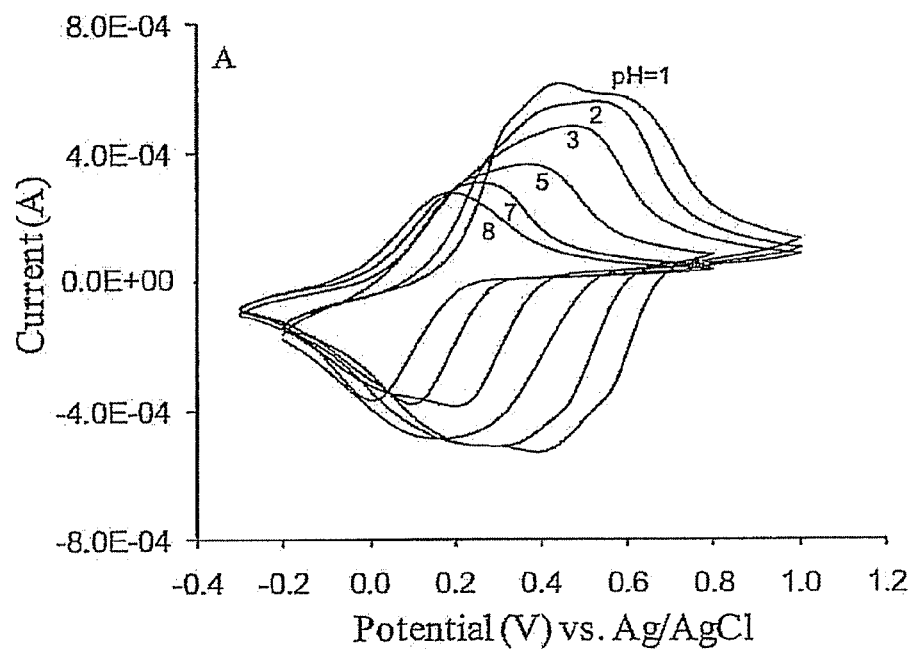
FIG. 11. Cyclic voltammograms at 100 mV/s (A) and $I_D$-$V_G$ characteristics at 5 mV/s (B) of PABA/phosphate coated IDA's as a function of pH of solution. The electrolyte pH solutions in the range of 1-8 are prepared using 0.5 M phosphoric acid and sodium bihydrogen phosphate.
Figure 11:
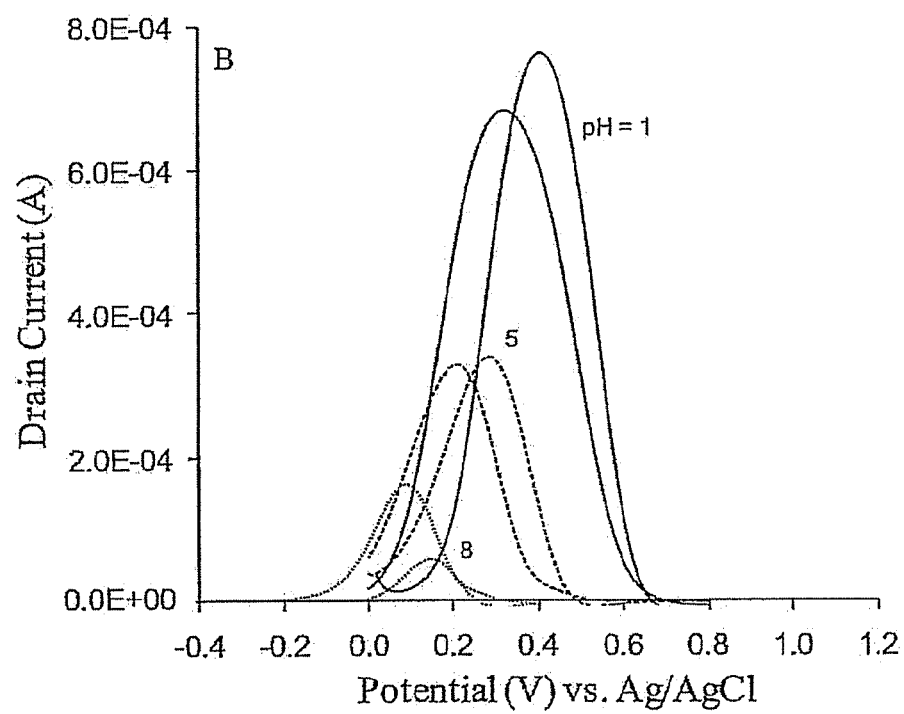

FIG. 11 shows the pH-dependent redox and in situ conductivity behavior of a PABA dispersion coated onto an IDA. The cyclic voltammograms of PABA in the pH range 1-8 shown in FIG. 11A suggest that PABA is redox active at neutral and above neutral pH. The oxidation and reductions peaks are dependent upon the pH of electrolyte solution. At pH 1-3, the presence of two sets of redox peaks is attributed to the facile conversion between oxidation states similar to unsubstituted PANI (Huang et al., 1986, *J. Chem. Soc., Faraday Trans.*, 82:2385) and previously reported for chemically and electrochemically prepared PABA under acidic conditions in the presence of fluoride (Deore et al., 2004, *J. Am. Chem. Soc.*, 126:52, Nicolas et al., 2000, *Eur. J. Org. Chem.*, 9:1703, Deore and Freund, 2003, *Analyst*, 128:803). However, above pH 3, only one set of redox peaks is observed, suggesting that the emeraldine form is not stable in this pH range and that PABA is directly converted from the fully reduced leucoemeraldine to highly oxidized pernigraniline form. This pH-dependent redox behavior is consistent with self-doped PABA in the presence of D-fructose (Deore et al., 2004, *Chem. Mater.*, 16:1427), sulfonated self-doped PANI (Lukachova et al., 2003, *J. Electroanal. Chem.*, 544:59), and PANI doped with phosphoric acid with long and short hydrophilic ethylene glycol segment (Luo et al., 2007, *Macromolecules*, 40:8132). Similar to these reports, the magnitude of peak current decreases as a function of pH of solution. However, the decrease in current observed for PABA in the pH range of 1-8 is far less than the reported one order decrease for sulfonated self-doped PANT (Lukachova et al., 2003, *J. Electroanal. Chem.*, 544:59) and the two order decrease for PANI doped with phosphoric acid with long and short hydrophilic ethylene glycol segment (Luo et al., 2007, *Macromolecules*, 40:8132). The cyclic voltammograms of PABA are reproducible and reversible in the pH range 1-8. These results suggest that self-doped PABA, involving an anionic tetrahedral boronate in the presence of phosphate and fluoride, is stable even in the absence of fluoride in electrolyte solution and during cycling and thus extending the electroactivity of PABA to neutral and above neutral pH.

FIG. 11B shows the $I_D$-$V_G$ characteristic of PABA in a potential range 0.0-0.8 V as a function of solution pH. Throughout the entire pH range, $I_D$-$V_G$ characteristics of PABA are reproducible from scan to scan. The $I_D$-$V_G$ characteristics show that the potential window of high conductivity is pH dependent similar to the redox behavior. Also, the width of conducting region is narrowed from 0.6 to 0.4 V for pH 1-8. The conductivity was calculated from the ohmic current flowing through the film via two working electrodes using the formula $\sigma = i_\Omega/EA$ S/cm, where $i_\Omega$ is the ohmic current, E is the voltage offset between the electrodes divided by the distance between them, and A is the total effective cross-sectional area between the two arrays of electrodes (Chidsey and Murray, 1986, *J. Phys. Chem.*, 90:1479). The cross-sectional area is determined by the thickness of the film (0.3 μm) and their total length (7.84 cm), leading to A=2.35 10-4 cm$^2$. The thickness of the film was calculated using the mass of the PABA, density, and electrode area. The measured spacing between the electrodes was 20 μm and the offset voltage between the electrodes of 50 mV. The conductivity of PABA reaches a maximum at a potential intermediate between the two states of being insulating fully reduced leucoemeraldine and fully oxidized pernigraniline form. At pH 1, the maximum conductivity of PABA is 0.14 S/cm at 0.4 V. The conductivity value decreased to 0.07 S/cm at 0.25 V and 0.03 S/cm at 0.1 V for pH 5 and 8, respectively. However, in the case of PANI, the reported maximum conductivity decreases almost 2 orders of magnitude from pH 0 to 4 (Zhang et al., 1997, *J. Electroanal. Chem.*, 440:35).

The PABA dispersions prepared in phosphoric acid in the presence of fluoride involves boron-phosphate interactions and formation of an anionic tetrahedral boronate group, which forms the basis of self-doped PABA. The highly conducting PABA dispersion with 25-50 nm size particles can be prepared without using surfactants or stabilizers as a template. Because of selfdoping, PABA dispersions have high electroactive and conducting stability in neutral and above neutral pH conditions. As a result, this material is an excellent candidate for pH, CO2, and biosensors as well as for formulations for coatings and inkjet printing.

Example 2

Material Preparation and Sensor Assembly

Carbon Dioxide Gas Concentrations

The correlation between different ppm levels of $CO_2$ and indication of infestation in grain stores has been established by Semple et al., (1988) (Table 2). Instruments capable of sensing $CO_2$ concentrations of 0.1% (1000 parts per million) in air in grain bulk will detect deterioration in 80% of deteriorating bulks in farm granaries (Muir et al., 1985, *Transactions of the ASAE* 28:1673-1675).

Simulation models of Singh (Jayas) et al. (1983, *Canadian Agricultural Engineering* 25:149-152) and experimental data of Muir et al. (Muir et al., 1985, *Transactions of the ASAE* 28:1673-1675) concluded that in the absence of prior knowledge of the location of potential deterioration of grain, a sensor capable of detecting $CO_2$ levels of 2 g/m$^3$ should be located near the centre of the bin.

$$ppmv = \frac{\left(\frac{mg}{m^3}\right)(273.15 + °C.)}{(12.187)(MW)} \quad (1)$$

where, ppmv=ppm by volume (volume of $CO_2$ per $10^6$ volumes of ambient air)

mg/m$^3$=milligrams of $CO_2$ per cubic metre of ambient air (2000 mg/m$^3$)

° C.=ambient air temperature in degrees centigrade

MW=molecular weight of $CO_2$ (44.01)

At 25° C., ppmv=1111.77.

Hence, for grain quality monitoring, the carbon dioxide sensor should be able to measure at least 1112 ppm to detect incipient grain spoilage.

TABLE 2

Carbon dioxide concentrations as an index of infestation in grain stores. Source: Semple et al., 1988, Proceedings of the Integrated Pest Management Strategies in Grain Storage Systems Conference, National Post Harvest Institute for Research and Extension (NAPHIRE), Department of Agriculture, June 6-18, Philippines.

| $CO_2$ Concentration (ppm) | Indication of infestation |
|---|---|
| 380 to 500 | Atmospheric concentration (no spoilage) |
| <1100 | Incipient spoilage |
| 1100 to 3500 | Slight insect infestation and (or) infestation of microorganisms |
| 3500 to 5000 | High insect infestation and (or) a higher infection of microorganisms |

TABLE 2-continued

Carbon dioxide concentrations as an index of infestation in grain stores.
Source: Semple et al., 1988, Proceedings of the Integrated Pest
Management Strategies in Grain Storage Systems Conference,
National Post Harvest Institute for Research and Extension
(NAPHIRE), Department of Agriculture, June 6-18, Philippines.

| $CO_2$ Concentration (ppm) | Indication of infestation |
|---|---|
| 5000 to 9000 | Severe spoilage and limit of dangerous storage conditions |
| >10000 | Highly unsuitable storage conditions |

Instrumentation

Gas Flow Management System

The gas flow management and the sensor evaluation system consists of a flow system to control the desired gas flow rates to the Teflon testing chamber, and a data collection system to record data from the sensor.

Figure 12:
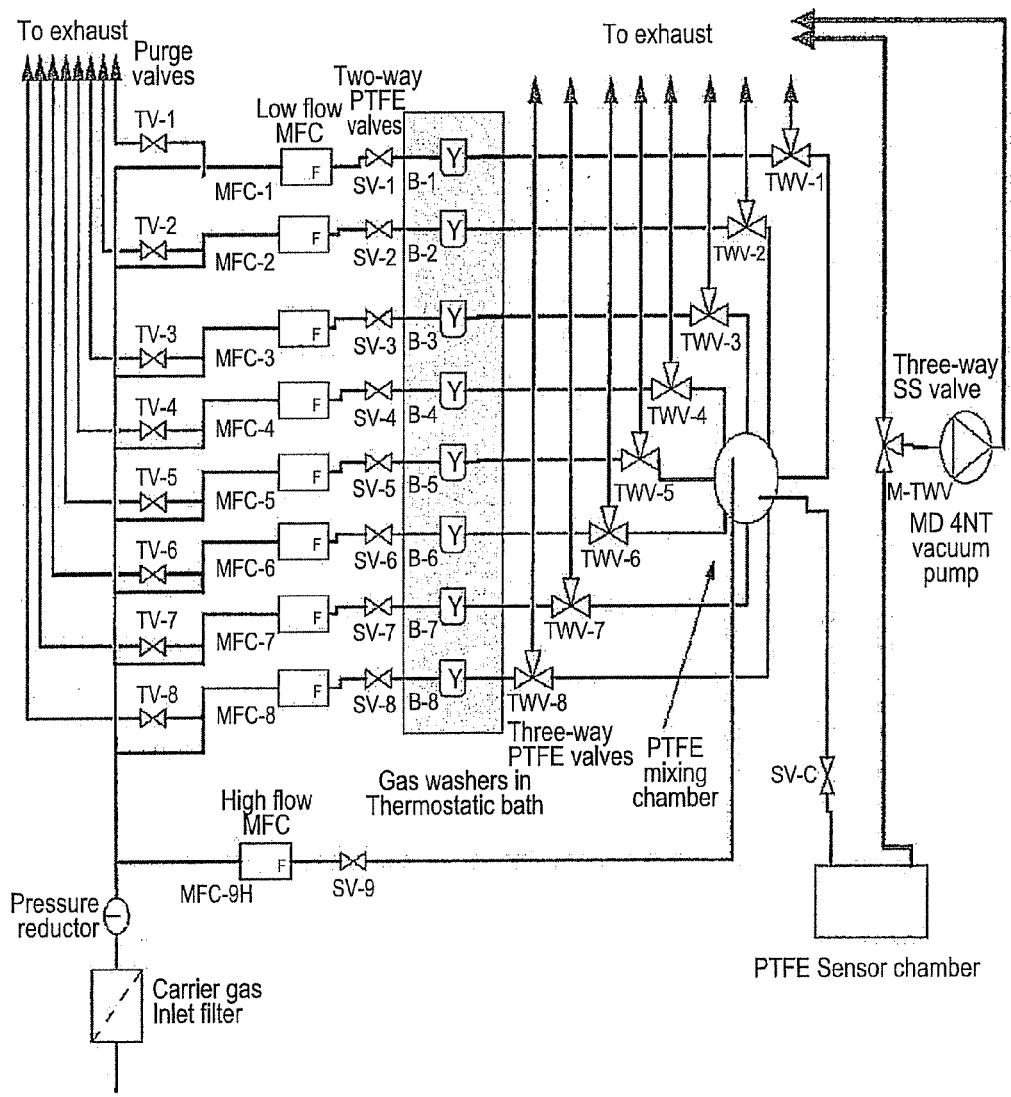
FIG. 12. Schematic diagram of the gas management system.

An automated vapour delivery system was built by Plasmionique Inc., Quebec, which can produce up to 8 vapours from solvents that are stored in 8 different glass bubblers. The flow rate of the vapours can be controlled using mass flow controllers and solenoid valves and be delivered to a Teflon gas mixing chamber and then delivered to the sensor-testing chamber. This system allows the user to produce mixtures of analyte at various flow rates and at desired concentrations of analyte solutions. The automated gas flow management system affords several advantages including unattended operation during long sequences of tests, reduced user exposure to toxic chemicals and precise data measurements. This automated system provides enough flexibility and capabilities to allow the users to build and design experiments with applications without the concern of limitations and/or expansion capabilities. This automated vapour delivery system was used for characterizing the developed carbon dioxide polymer sensors. A schematic of the custom built gas flow management system (Plasmionique Inc., Quebec) is shown in FIG. 12.

Data Collection System

The data collection system used for characterization of the $CO_2$ sensor consisted of an Agilent 34980A Data Acquisition Switch Unit (Agilent Technologies, Inc., Santa Clara, Calif.). The dc resistance of the sensor was read sequentially by the Agilent data acquisition unit. The control computer was interfaced with data collection system through an IEEE general purpose interface board (GPIB). The resistance data were initially stored in the data acquisition unit and once a complete set of data were recorded, the GPIB communications protocol sent the data to the control computer where the data were stored in a tab-limited text file. The gas flow management system and the data collection system were interlinked and connected through a LabVIEW (National Instruments Corporation, Austin, Tex.) algorithm to efficiently control and simultaneously record the gas mixture readings and the sensor response output values.

Commercially available gas cylinder (Praxair, Edmonton, Canada) with a blend of $CO_2$/air mixture of 9820 ppm concentration and a nitrogen cylinder of ultra high purity (99.99%) were used for the measurements. To achieve the required ppm levels of $CO_2$ concentrations, gas from 9820 ppm level was diluted to appropriate concentrations by mixing and varying the gas flow rate from the nitrogen cylinder. For example, a flowrate of 100 sccm of 9820 ppm and 100 sccm of nitrogen in the Teflon mixing chamber measured at the same pressures and temperatures produced 200 sccm of 4910 sccm of $CO_2$ (Table 3). In a similar fashion, desired levels of $CO_2$ concentrations were achieved by mixing various levels of nitrogen and $CO_2$ from a 5000 ppm $CO_2$ in air.

TABLE 3

Gas flow mixture ratio of nitrogen (99.99%) and carbon dioxide (9820 ppm) to achieve desired $CO_2$ concentrations.

| MFC 8 (sccm) ($CO_2$) | MFC 9 (sccm) (N2) | MFC 1 (sccm) (Water) | $CO_2$ ppm |
|---|---|---|---|
| 7.8 | 192-X | X | 382 |
| 20 | 180-X | X | 982 |
| 30 | 170-X | X | 1473 |
| 50 | 150-X | X | 2455 |
| 60 | 140-X | X | 2946 |
| 75 | 125-X | X | 3682 |
| 100 | 100-X | X | 4910 |

X indicates the flow rate of nitrogen inside bubbler containing water.

The sensor to be characterized was placed inside a Teflon (PTFE) sensor testing chamber and exposed to the gaseous mixtures of $CO_2$ in nitrogen delivered via the gas flow management system.

Materials

The reagents, chemicals and adhesives including 3-aminophenylboronic acid, polyaniline, phosphoric acid, sodium fluoride, ammonium persulfate, poly vinyl alcohol, potassium chloride, nafion, cyanoacrylate (Permabond 105), poly (vinyl chloride), used for the sensor construction were of analytical grade and purchased from Sigma-Aldrich Inc (St. Louis, Mo.). All aqueous and buffer solutions were prepared with 18.2 MΩ quality deionized water using an ultrapure water system (Millipore Corporation, Billerica, Mass.). Carbon dioxide porous PTFE membranes with 60 μm thickness and with average pore diameter of 0.2 μm were acquired from Thermo Scientific (Waltham, Mass.). Chemically resistant perfluoroelastomer O-rings of 0.3 mm diameter and 0.1 mm wall thickness used for mounting the PTFE gas permeable membrane were purchased from Fisher Scientific (Pittsburgh, Pa.).

PABA Film Synthesis

The 3-amino phenyl boronic acid substituted polyaniline (PABA) film was synthesized as described in Example 1. The PABA dispersion solution was synthesized chemically using 10 mM 3-APBA (monomer)+50 mM NaF+5 mM ammonium persulphate (oxidant) in 0.1 M phosphoric acid. The chemical synthesis of PABA polymer is easily water dispersible, and hence it facilitates to form smooth, adherent and uniform thin films on the electrode surface. The particle size of PABA is in the range of 50-100 nm and provides a higher surface area for sensing.

Sensor Construction

Figure 15:
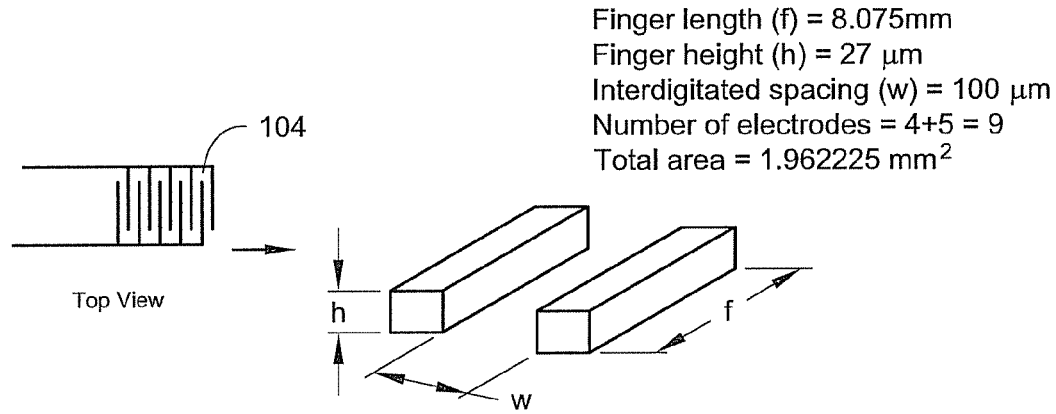
FIG. 15. Schematic of interdigitated gold electrodes.
Figure 16:
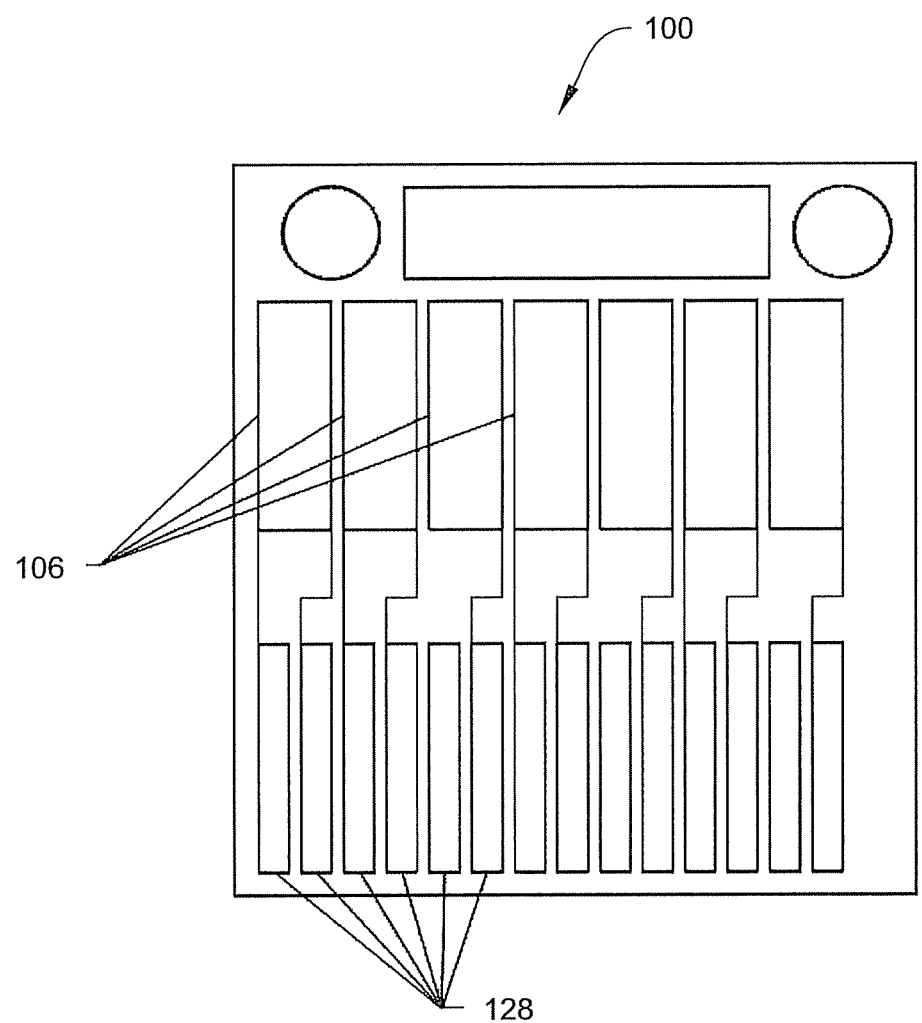
FIG. 16. One embodiment of a sensor array.

A cross-sectional and a schematic side view of the constructed sensor assembly are shown in FIGS. 13 and 14, respectively. Gold interdigitated array electrodes (IDAs) to be used as the sensor substrate platform, deposited on a 1 mm thick printed circuit board (PCB) was designed upon consultation with Iders Inc, Winnipeg, MB. The sensor chip was fabricated by Dynamic & Proto Circuits Inc, Stoney Creek, ON. Each sensor chip has seven sensor elements (detectors) (FIG. 16). The dimensional details of the interdigitated electrode are shown in FIG. 15.

The PABA was used as the sensing material in preparing the electrically conductive region for the sensor. A 2 μL PABA solution (10 mg/ml) was deposited on the IDAs through a micropipette as a physical dispersion process and was allowed to dry for 20 min. A 2 μL of Nafion solution was superimposed directly on top of the PABA thin film in the electrically conductive region of the sensor. The solution was then allowed to evaporate in air at 25° C. and a dried residue was left to form the conductive sensing material.

Similarly, an internal electrolyte-hydrogel solution prepared from an aqueous solution of 99.99% hydrolyzed polyvinyl alcohol (0.5 wt/vol %) with 0.0001 M sodium bicarbonate and 0.0001 M potassium chloride was also used for building the sensor assembly. A 4 µL of the internal electrolyte/hydrogel composite was superimposed directly on top of the PABA thin film in the electrically conductive region of the sensor. The solution was allowed to evaporate and a dried residue was left to form the ion-selective gas permeable membrane.

The PTFE membrane was applied directly on top of the dried residue of the internal electrolyte (Nafion or PVA electrolyte-hydrogel membrane) with the aid of an O-ring. The membrane was cut into circular shapes of approximately 11 mm diameter and was attached to the O-rings by applying small amounts of cyanoacrylate adhesive. The O-ring with the mounted membranes was glued carefully to the PCB substrate of the sensor assembly, forming a cavity with the electrolyte/hydrogel composite and the PABA thin film below the membrane. Care was taken to apply the adhesive only on the rim of the O-ring and thereby avoiding the adhesive contact with the sensing material. The gap between the gas permeable membrane and the surface of the electrolyte/hydrogel composite was kept at a minimum distance (<0.2 mm) using an O-ring to maintain the thin layers of the electrolyte and sensing material.

Humidity Setup

The humidity of the various concentrations of $CO_2$ gases were increased from 20 to 80% relative humidity by bubbling through water. The controlled humidified analyte gases at room temperature (25±2° C.) were introduced steadily at a constant flow rate from the bubblers into the flow cell. The actual humidity of the analyte gas was monitored by a calibrated humidity sensor (Model HIH-4000, Honeywell Sensing and Control, Golden Valley, Minn.).

The HIH-4000 sensor contains a capacitive sensing die, set in thermoset polymers that interact with platinum electrodes. The HIH-4000 sensor has an integrated circuit which when supplied with an excitation voltage produces a DC voltage output which is proportional to the relative humidity. The HIH-4000 sensor was connected to an Agilent data acquisition 37970A unit (Agilent Technologies, Inc., Santa Clara, Calif.) through a screw terminal which supplied the excitation voltage. The calibration of HIH-4000 sensor was done against known concentrations of standardized KOH solutions of different concentrations. The display output from the data acquisition system was calibrated against the readings, with the slope and offset (Greenspan, 1977, *Journal of the Research National Bureau of Standards-A, Physics and Chemistry* 81(1):89-96; Solomon, 1951, *Bulletin of Entomological Research* 42:543-554).

Figure 17:
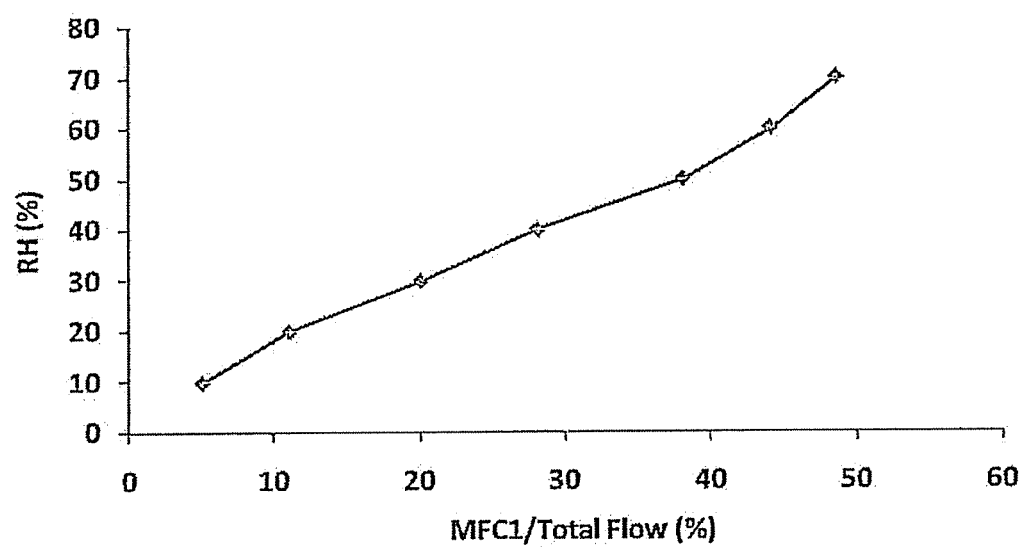
FIG. 17. Relationship between humidity level and flowrate of nitrogen through MFC1 and MFC9.

The relationship between humidity level and ratio of flow rate passing through bubbler containing water to the total flow rate is shown in FIG. 17. For example, gas flow of 97 sccm of $N_2$ through bubbler by MFC1 and 103 sccm of $N_2$ from MFC9 into the mixing chamber will produce 70% RH at 25° C.

Results and Discussion

Sensor Principle

The sensing mechanism is based on the interconversion between conducting emeraldine salt form and the insulating emeraldine base form of polyaniline and PABA through protonation and deprotonation.

When the analyte (gaseous $CO_2$) permeates through the gas permeable membrane, $CO_2$ reacts with water from PVA to create a bicarbonate ion ($HCO_3^-$) and a proton, which protonates the polyaniline. When the $CO_2$ diffuses through the gas-permeable membrane, the following equilibria are sequentially established (Jensen and Rechnitz, 1979, *Analytical Chemistry* 51(12):1972-1977).

$$CO_2(aq) + H_2O \rightleftharpoons H_2CO_3 \quad (2)$$

$$H_2CO_3 \rightleftharpoons H^+ + HCO_3^- \quad (3)$$

$$HCO_2^- \rightleftharpoons H^+ + CO_8^{2-} \quad (4)$$

As the $CO_2$ partial pressure increases, the conductivity increases due to increase in the amount of protonation. This changes the pH of the internal electrolyte. The change in pH is related to the potential of the PABA thin film through the Nernst equation (Eq 5). The potential changes linearly with the pH and thereby the concentration of the analyte can be measured.

$$E = E^\circ - \frac{0.0591}{z} \log \frac{a_{Red}}{a_{Ox}} \quad (5)$$

where z is the number of moles of the electrons involved in the reaction, a is the chemical activity for the relevant species, Red is reduction and Ox is oxidation.

Figure 18:
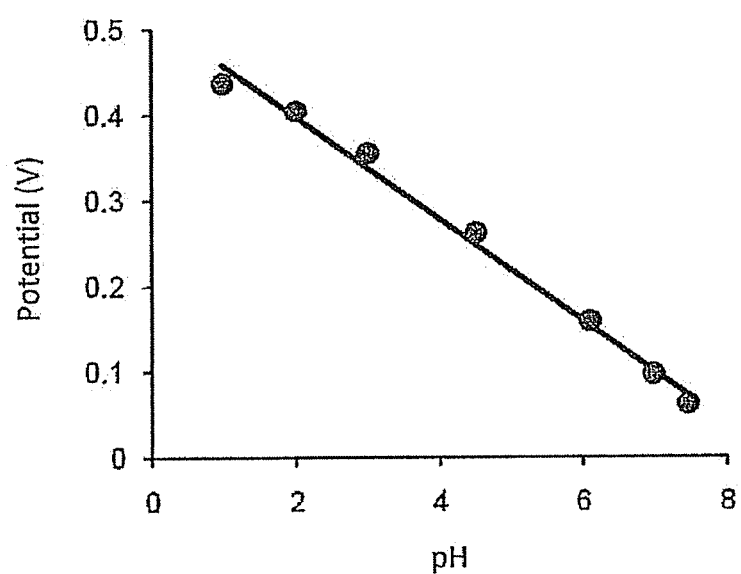
FIG. 18. Open-circuit potential response of PABA film as a function of pH of solution.

Nernst equation relates the potential of electrochemical cell (or sensing assembly) as a function of concentration of ions in the reaction. FIG. 18 illustrates the potentiometric response of PABA to changes in $H^+$ ion concentration revealing a Nernstian response slope of m=−59 mV $pH^{-1}$ for buffer solutions from pH 1 to 8.

Sensing measurements were done at different potentials using amperometry at the working electrode. For all the amperometric measurements, a constant potential of 0.01 V (optimized potential) on the sensor was applied which facilitated a wider linear range, steady-state, response current output.

Figure 19:
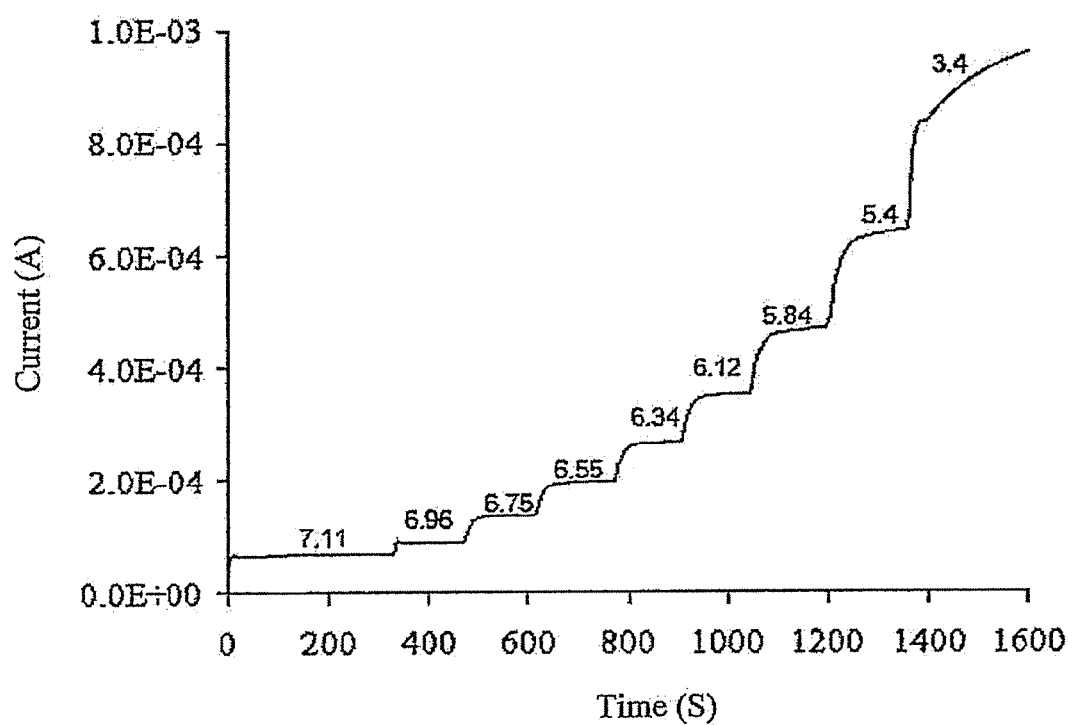
FIG. 19. Amperometric measurement of PABA film at 0.2 V as a function of pH of solution.

FIG. 19 shows typical response behaviour of the PABA film to change in pH. A 3 µL PABA solution (10 mg/ml) deposited and dried on the gold IDA was characterized for its sensitivity to change in pH in 0.1 M KCl and sodium phosphate buffer solution. The change in pH of the buffer solution was achieved by adding 1 M $H_2SO_4$. The PABA showed linear response in the near neutral pH range of 4-7, and therefore, was selected for use as sensing material for constructing $CO_2$ sensor. The results of this experiment confirmed the desired pH response properties of PABA thin film such as stability, response time and linear range.

The sensors were placed in the Teflon test chamber and were exposed, alternately, to clean dry background air and air containing analyte. The sensor exposures alternated between 5 min of clean background air and 5 min of different analyte concentrations for each analyte concentrations. Baseline resistance for each sensor was established by flowing background air (air containing 380 ppm of $CO_2$) and at 0% humidity prior to various nitrogen and $CO_2$ exposure levels. Sensor data were recorded as resistance versus time and the events such as an exposure to various $CO_2$ levels or a change in humidity or temperature were analyzed as normalized changes in resistance (αR/R0).

$$\frac{\Delta R}{R\max} = \frac{(R\max - R0)}{R0} \quad (6)$$

Rmax=sensor resistance at the plateau of the response
R0=resistance prior to the event The displayed graph data were processed using background determination as R0 prior to an exposure of analyte to correct for baseline drift.

PABA Film Thickness

| | |
|---|---|
| Density of PABA film | = 1.5 g/cm$^3$ |
| Mass of the film = 3 μL | = 10 mg/ml |
| Working electrode area | = 1.96 mm$^2$ = 0.0196 cm$^2$ |
| Density | = Mass/Volume |
| Average thickness of the film (cm) | = mass (g)/(Surface area (cm$^2$) + Density * (g/cm$^3$) |
| | = 0.003/(0.0196 + 1.5) |
| | = 0.00197 cm |
| | = 19.74 micron thickness |

This calculation of average film thickness is prone to errors considering the coulombic efficiency, sticking coefficient, substrate tilt angle etc.

Performance of PABA Sensor without Electrolyte

For functional feasibility, the sensor industry prefers solid electrolyte over liquid electrolyte to maintain compactness of sensor cells considering the size of packaging components, leakage, and drying up of liquid electrolyte under high humidity/temperature conditions. Among the solid electrolyte polymers known, Nafion is the best in terms of conductivity and chemical resistance properties (Viswanathan and Helen, 2007, *Bulletin of the Catalysis Society of India* 6:50-66; Hu et al., 2008, *DMFCs Journal of Applied Electrochemistry* 38(4):543-550). Nafion functions as an acid catalyst due to strongly acidic properties of the sulfonic acid group, and also as an ion exchange resin. The sulfonic acid groups in Nafion have a very high water-of-hydration. Interconnections between the sulfonic acid groups lead to rapid transfer of water through the Nafion. Nafion has been widely used as a proton exchange membrane in polymer electrode fuel cell applications.

The sensor electrodes prepared with only PABA and without Nafion were exposed to different concentrations of $CO_2$ at various humidity levels.

Figure 20:
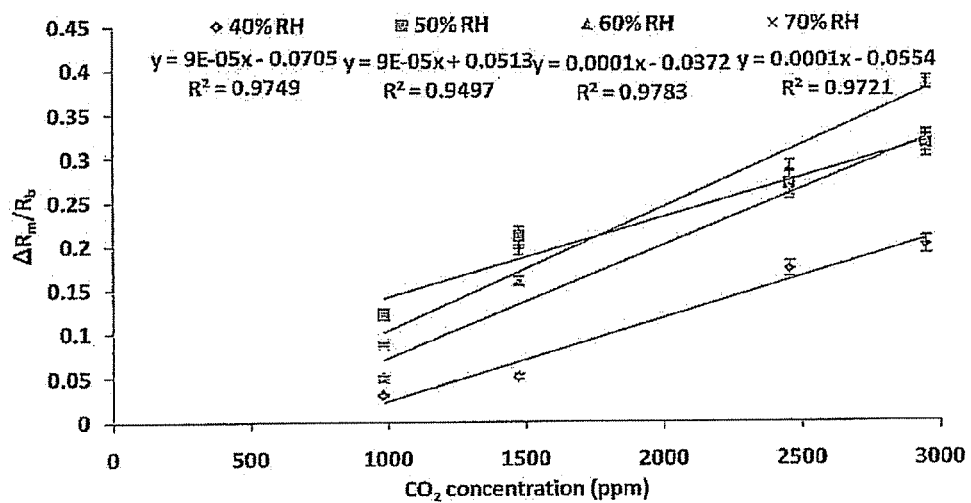
FIG. 20. Response of PABA sensor electrodes (without electrolyte) to various concentrations of $CO_2$ at different humidity levels and at 25° C.

No response was observed from the electrodes below 40% RH. For protonation to occur to facilitate the exchange of ions upon exposing to analyte, PABA requires water molecules. So, at higher humidity levels above 40% RH, the PABA was able to respond to analyte concentrations (FIG. 20) and this could be due to the absorption of water molecules from air. The resistivity was seen to increase slightly from 40% to 70% RH. The baseline resistance of the sensor during background airflow increased from 4300 ohms at 40% RH to 5750 ohms at 70% RH. The sensors exhibited quick response for changing humidity and the response and recovery times were of the order of few seconds. The variation in the resistance parameters was nearly linear (curvilinear) and was repeatable. The sensor electrodes show a saturation effect at 2455 ppm.

Effect of Humidity

Figure 21:
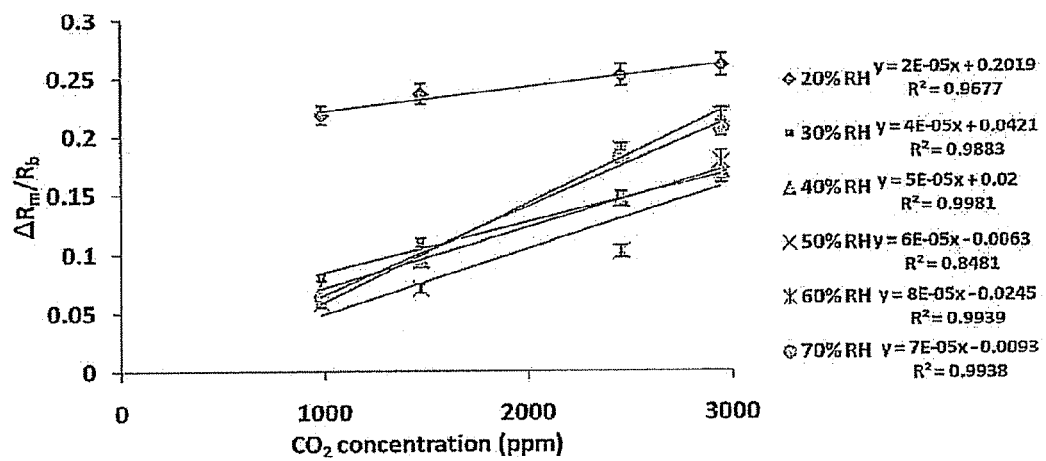
FIG. 21. Variation of resistance with change in relative humidity (%) for PABA-Nafion sensor at 25° C.

The results of the relationship between resistance and $CO_2$ concentration for the PABA-Nafion sensor under various humidity levels are shown in FIG. 21.

The humidity has less pronounced effect on the performance of the PABA Nafion sensor. It has been reported (Skotheim et al., 1998, Handbook of conducting polymers. Boca Raton, Fla.: CRC Press) that the conductivity of conducting polymers increases when the film absorbs the moisture. The resistance value of PABA decreased with humidity level due to the possibility of proton exchange between the water molecules and the protonated and the unprotonated forms of PABA.

PABA-Nafion sensor showed two step sensing response to humidity levels. The resistance value of the sensor electrodes decreased when RH increased from 20 to 50% indicating that the water molecules might have been absorbed by the PABA film. The charge transfer process of conducting species with water molecules resulted into the decrease in the resistance value. The resistance values of the sensor increased when RH increased from 50% to 70%. The mechanism of charge transfer process may be different for the humidity levels between 50 to 70% RH. The deviation in the linearity could be attributed to the size of the pores of polymer. Similar deviation in the linearity behaviour was observed by Parvatikar et al. (Parvatikar et al., 2006, *Sensors and Actuators B* 114:599-603) in a PANI/$WO_3$ composite sensor when exposed to humidity levels between 20 to 90% RH. The polymer might swell due to water absorption and there may be breakdown or increase in contact between the dispersed conductive nano particles affecting the resistance value with the change in humidity. The polymer backbone might swell due to the change in humidity and the pathways inside the film might be saturated with water leading to change in the diffusion rate of gases into the polymer matrix. As the humidity increases from 20% to 50% RH, there may be more hydrogen carbonate ions and protons produced on the PABA film, thus lowering the resistance of the film. Above 50% RH level, the pores might be saturated causing a change in diffusion pathways. The variation in the resistance parameter was curvy-linear and repeatable. The film's response to change in analyte concentrations at various humidity levels was very stable until 70% RH and becomes noisy above 70% RH. At humidity levels above 70% RH, the sensors might still perform well when provided with a rugged membrane protection and a proper sensor packaging. Irrespective of the change in resistance values at different humidity levels, all the PABA-Nafion sensors responded to various levels of $CO_2$ concentrations up to 2455 ppm.

Figure 22:
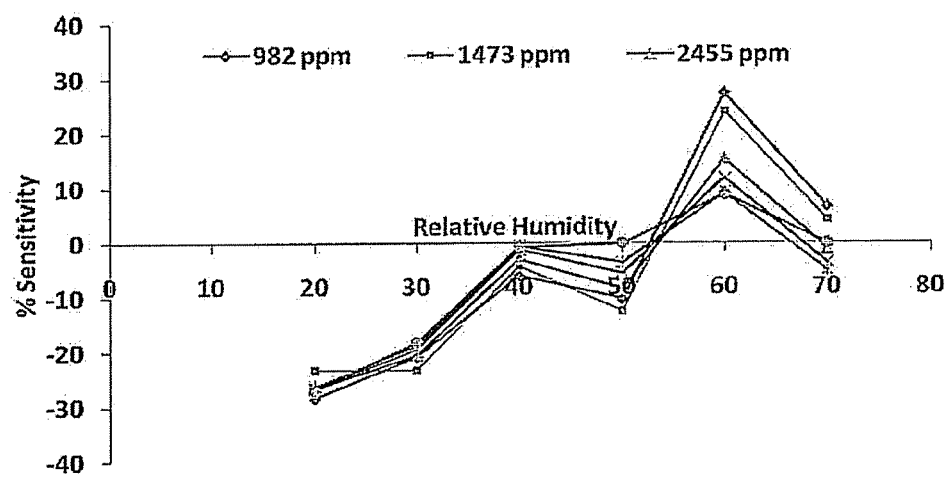
FIG. 22. Variation of sensitivity with change in relative humidity (%) for PABA-Nafion sensor at 25° C.

The variations in the resistivity as a function of relative humidity value for the PABA sensor is depicted in the FIG. 22.

The percentage sensitivity as a response to humidity is defined as:

$$S = \left[\frac{(RH2 - RH1)}{RH1}\right] \times 100 \quad (7)$$

where RH2 is the resistivity of the PABA sensor for humidity at level 2, and RH1 the resistivity of the PABA sensor for humidity at level 1.

PABA-Nafion sensor's sensitivity shows two step responses at various humidity levels. The behavior of the sensors is almost linear from 20 to 40% RH (FIG. 21). A saturation effect is observed between 40 to 50% RH and the sensitivity of the sensor decreases above 60% RH. The conductivity of PABA increases when the sensing material absorbs the moisture. With the adsorption of water molecules at increasing humidity levels, the resistance decreases from 20 to 40% RH. Partial charge transfer process of conducting species with water molecules might result into the decrease in the resistivity. This mechanism might be different at higher humidity levels.

The decrease in the resistivity value or the increase in conductivity could also be attributed to the geometry of the polymer and the charge transfer across the polymer chains. The sensor electrodes display a saturation effect above 2455 ppm of $CO_2$. The sensor's working principle depends on the extraction of ions and electrons and due to the change in protonation state from the PABA film. With larger porous structure, the PABA film will provide a large reaction surface and inner space for the electrolyte penetration into the film. So, this might shorten the diffusion pathways for the counter ions and lead to quicker response time. Changing the morphology of films by creating a higher surface area through nanorods or nanofiber structures in the polyaniline film might enhance the sensitivity and response time of the sensor (Virji et al., 2004, *Nanoletters* 4:491-496).

Effect of Temperature

The influence of temperature on the performance of the constructed sensors was evaluated by allowing the analyte gas to pass through a copper coil immersed in heated water bath circulator (Model 12108-20 Cole-Parmer Instrument Company, Vernon Hills, Ill.). The temperature range was maintained from 25° C. to 55° C. The sensor chip was also tested at various $CO_2$ levels after storing the chip at −25° C. for 48 h and then at room temperature for about 2 h before placing it in the testing chamber. For −25° C., the measurements were carried out when the temperature of the testing chamber was maintained at +25° C. The temperature of the analyte gas inside the testing chamber was monitored using a temperature sensor (Model 44034 Omega Precision Thermistor, Omega Engineering Inc, Stamford, Conn.).

Figure 23:
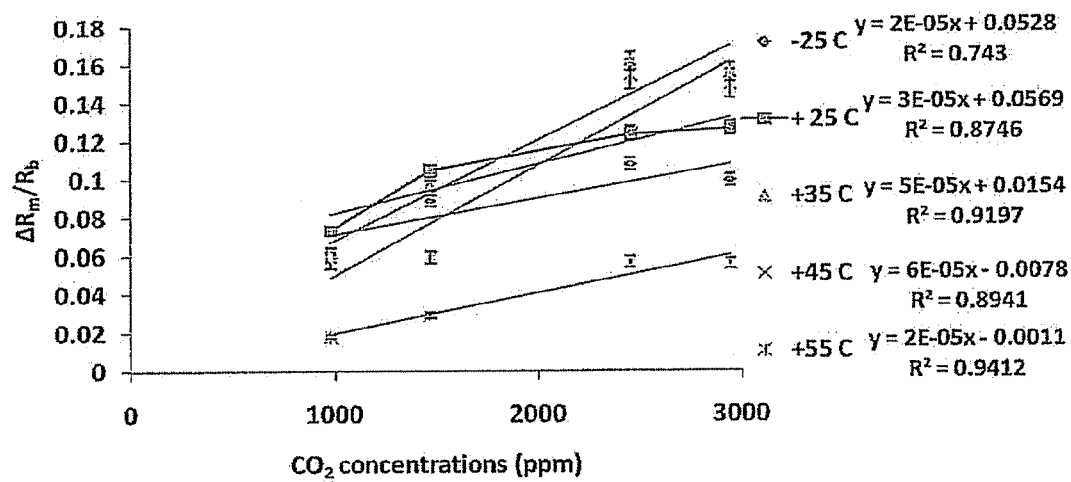
FIG. 23. Variation of resistance with change in temperature (° C.) for PABA-Nafion sensor at 50% RH level for 7 replicates.

For the PABA-Nafion sensor, the resistance value increased from 5382 to 6000 ohms when the temperature increased from −25° C. to +25° C. and decreased from 6000 to 1044 ohms when the temperature increased from 25° C. to 55° C. when exposed to 2455 ppm $CO_2$. Experiments were conducted by changing the order of heating the $CO_2$ gas flow and similar trend was observed indicating that the phenomenon is reversible irrespective of the temperature order. The decrease in the resistance value upon increase in temperature (FIG. 23) may be due to the loss of protonation and expulsion of water molecules from the polymer composite. In terms of thermal stability, the influence of the acid used for the protonation of PANI is more than the polyaniline backbone itself, because polyaniline has the ability to sustain exposure to an elevated temperature of 173° C. without decisive damage (Prokes and Stejskal, 2004). Thermogravimetric analysis of PABA by Yu et al. (2005) proves that the thermal stability of PABA is greater than that of other self-doped forms of polyaniline. When exposed to greater than 400° C., polyaniline experiences complete decomposition of the backbone, while PABA remains intact and possesses high level of conductivity. The increase in resistance value with temperature increase from −25° C. to +25° C. can be explained by the change in the morphology of the film and the restriction of the transportation of charge carriers.

The percentage sensitivity as a response to temperature is defined as:

$$S = \left[\frac{T2-T1}{T1}\right]100 \qquad (8)$$

where T2 is the resistivity of the PABA sensor for temperature level 2, and T1 is the resistivity of the PABA sensor for temperature at level 1.

Figure 24:
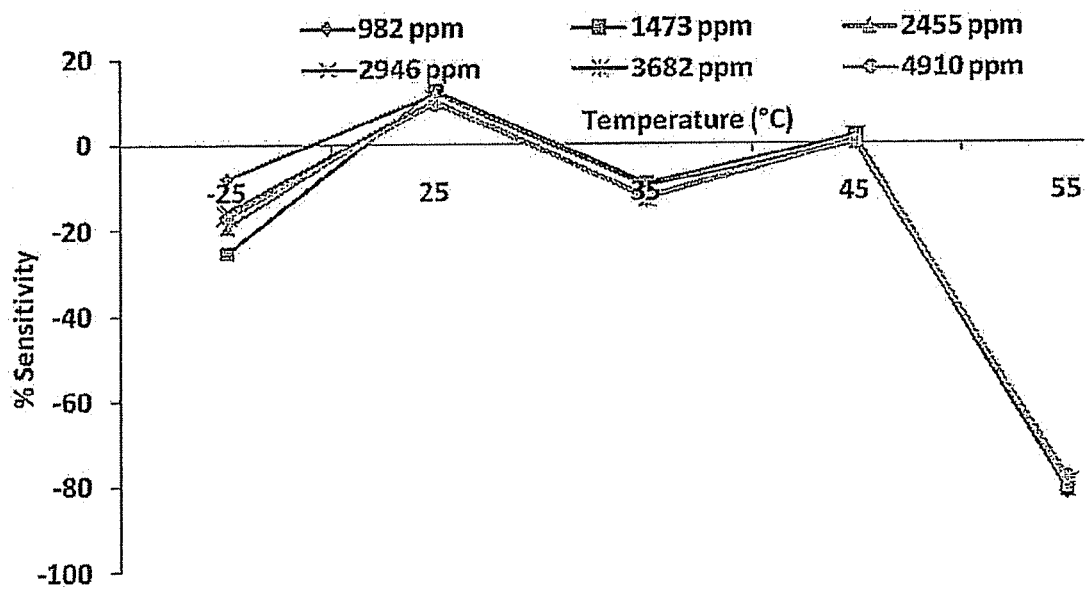
FIG. 24. Variation of sensitivity with change in temperature (° C.) for PABA-Nafion sensor at 50% RH level for 7 replicates.

PABA-Nafion sensor's sensitivity shows saturated response to analyte between −25° C. to 45° C. (FIG. 24). The sensitivity of the sensor decreases above 45° C.

The conductivity of PABA decreases with loss of moisture from the sensing material. The chain alignment of the polymer and the charge transfer between the polymer chains and dopants might be influenced by thermal curing leading to decrease in resistance value. When polyaniline is serving as a donor, the thermal excitation of electrons in polyaniline facilitates the charge transfer. However, if polyaniline assumes the role of an acceptor, the charge transfer becomes less efficient at higher temperatures (Li et al., 2004). The sensor did not respond to various $CO_2$ concentrations and the response became noisy above 55° C. To assess the influence of temperature, experiments were conducted at 50% RH for measurements at +25° C. As the temperature increased from −25 to +55° C., the water molecules in the air might be reduced to a greater extent.

Repeatability and Reproducibility

Figure 25:
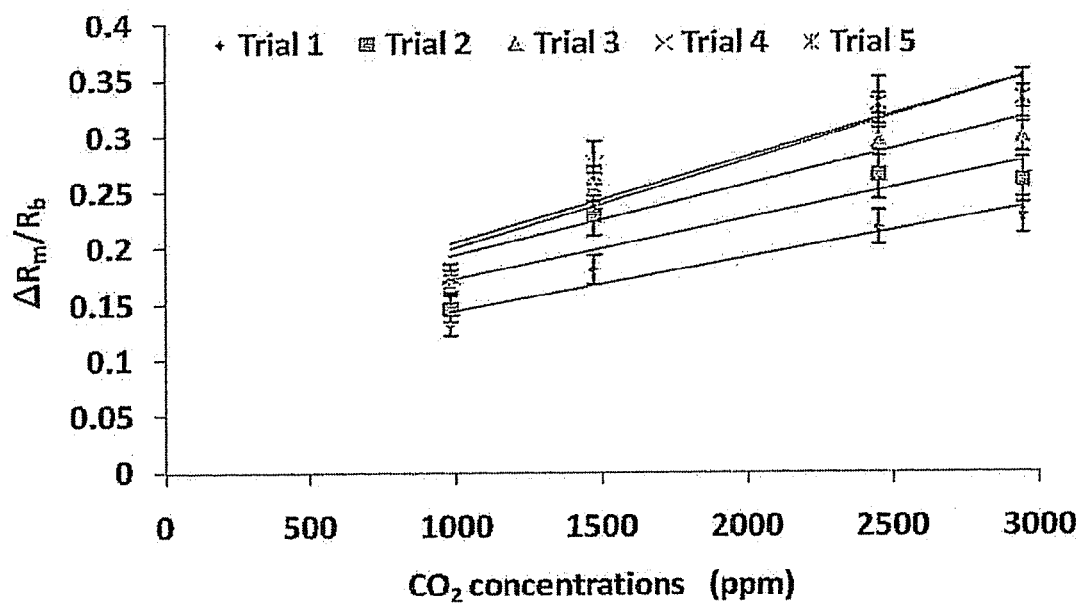
FIG. 25. Response of PABA-Nafion Sensor Chip #64 (5 trials, same electrode) to various concentrations of $CO_2$ at 40% RH and at 25° C.
Figure 26:
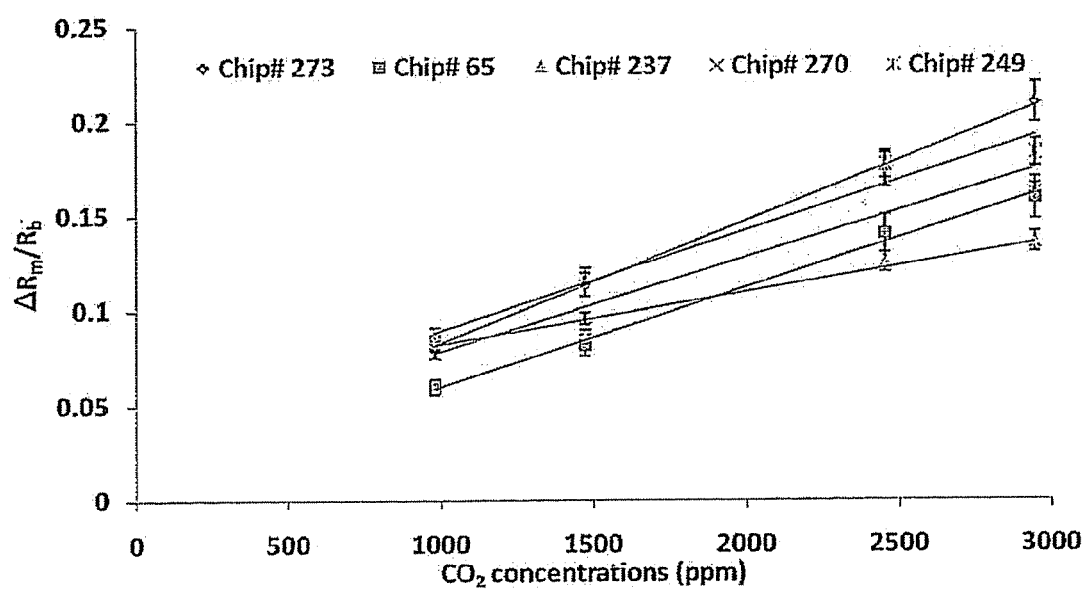
FIG. 26. Response of 5 different similarly constructed PABA-Nafion sensors to various concentrations of $CO_2$ at 40% RH and at 25° C.

Sensor repeatability refers to the successive runs made using a single sensor to evaluate discrepancies in its response. Sensor reproducibility refers to the sensor variations in response between individual chips of a batch of similarly constructed sensors. The repeatability of the sensor was studied by using the same sensor to repeatedly (five times) measure the response to different $CO_2$ concentrations (FIG. 25). At the same time, the reproducibility of the sensor was studied by using five similarly constructed sensors to measure the response at various $CO_2$ gas levels (FIG. 26).

In the reproducibility study, the same response trend was observed for all of the sensors on the same chip. Each sensor chip had seven sensors and the response of the sensors is shown in FIG. 25. The response of the sensors was not stabilized initially, but over the course of time, it stabilized. The relative standard deviation (R.S.D.) for repeatability and reproducibility of the sensor was 8 and 11%, respectively. Variation in the response of the sensor could be due to the construction variation and operational variation. The sensitivity got better with time/exposure as trial 4 and trial 5 responses are nearly overlapping. The same trend was observed for all sensor electrodes in different chips (data not shown).

To study the human-error prone fabrication procedures and to observe the replication on reproducibility, sensors were prepared by another researcher (operator 2) with similar construction parameters. Operator 2 prepared the sensor electrodes using physical dispersion process and tested the same under various concentrations of $CO_2$ at 50% RH.

Figure 27:
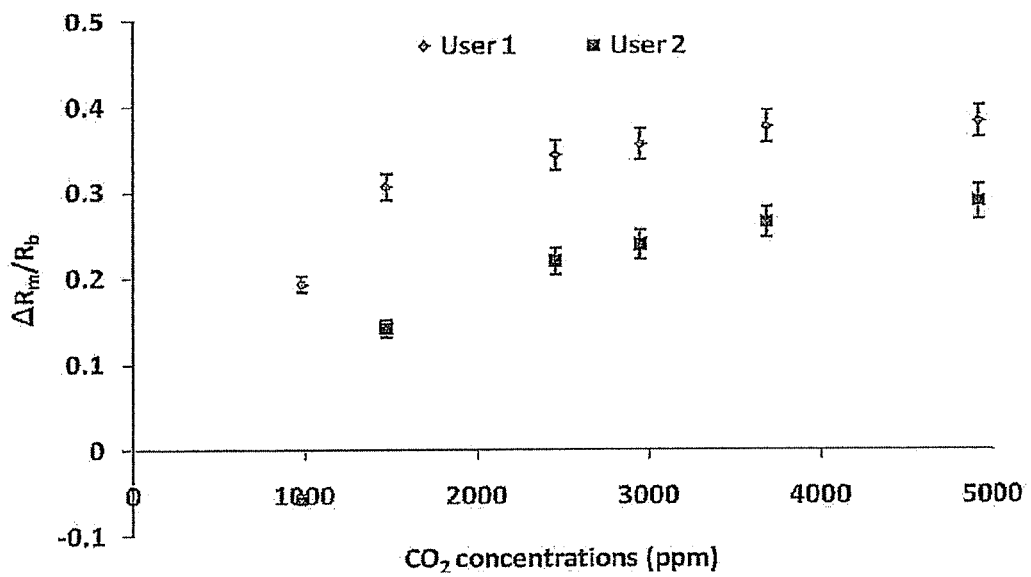
FIG. 27. Response of similarly constructed PABA-Nafion sensor chips by 2 different persons to various concentrations of $CO_2$ at 40% RH and at 25° C.

Variation between the sensor responses prepared by 2 different researchers could be due to the operational and constructional parameter variations. The relative standard deviation was 6% and 7% for the operator 1 and operator 2, respectively, which is less than 11%, the reproducibility R.S.D of the sensor prepared by user 1 (FIG. 27). Hence, the human-error prone fabrication errors are not significant. Performance wise, sensors prepared by user 1 and user 2 behaved in a similar fashion as the saturation effect was observed above 2455 ppm of $CO_2$.

Dynamic Characteristics

Sensitivity, linearity, accuracy, drift and hysteresis properties have transient effects that are settled to their steady state and are the static characteristics of sensor. The experimental results on the effect of humidity and temperature indicate that the response of the PABA-Nafion sensor to various levels of $CO_2$ is linear up to 2455 ppm and above that a saturation effect is observed. Prior to actual measurements, the sensor was exposed for 20 min in the background gas flow to achieve stabilized response and to reduce associated drift. The repeatability and reproducibility experiments results show that the PABA-Nafion sensor is accurate with higher sensitivity. A sensor's sensitivity indicates how much the sensor's output changes upon exposure to analyte. Drying the sensor electrodes after material deposition over 30 min reduced the drift to a large extent.

Figure 28:
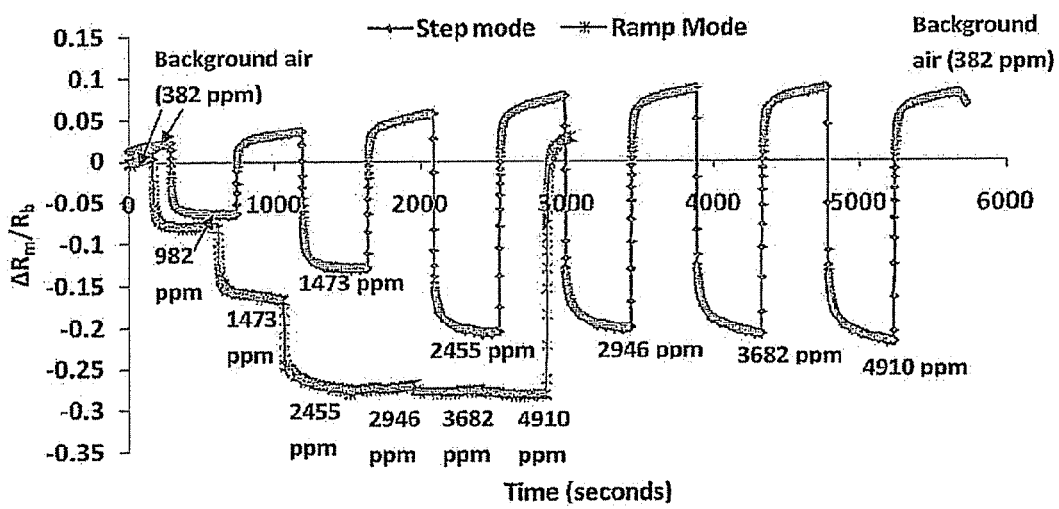
FIG. 28. Response of the PABA-Nafion sensor operated in step and ramp mode to various concentrations of $CO_2$ and subsequent exposure to background air at 40% RH and at 25° C.
Figure 29:
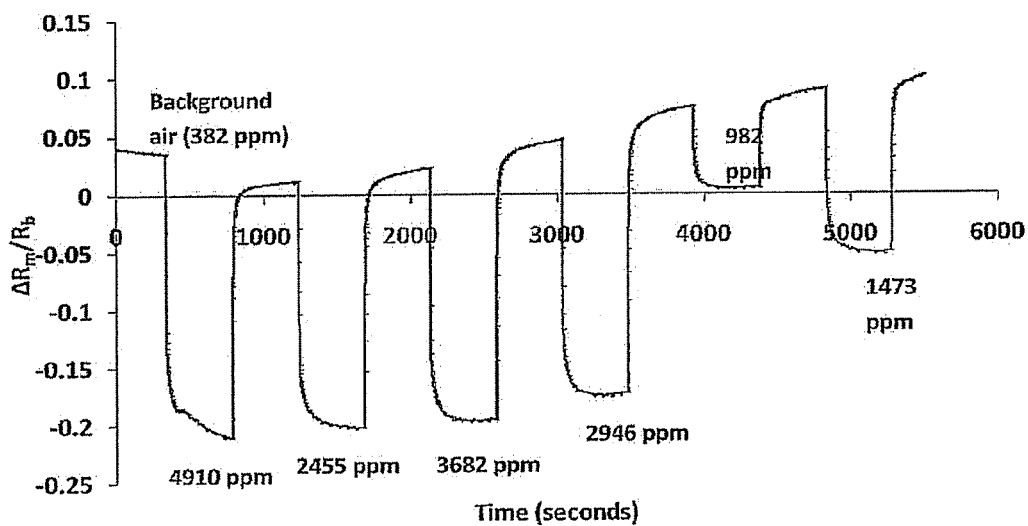
FIG. 29. Response of the PABA-Nafion sensor operated in random mode to various concentrations of $CO_2$ and subsequent exposure to background air at 40% RH and at 25° C.

The dynamic characteristics of a sensor are determined by analyzing the response of the sensor to variable input of analyte ($CO_2$) concentrations such as step mode, ramp mode (FIG. 28) and random measurement (FIG. 29). Characterization of the PABA-Nafion sensor's dynamic response was evaluated by comparing the step mode and ramp mode measurement. The ramp mode response curve shows that the PABA-Nafion sensors did not respond to $CO_2$ levels above 2455 ppm. The step or pulsed mode measurement shows that the response curve was reversible upon exposure to background gas.

Evaluation of Gas Permeable Membrane

Figure 30:
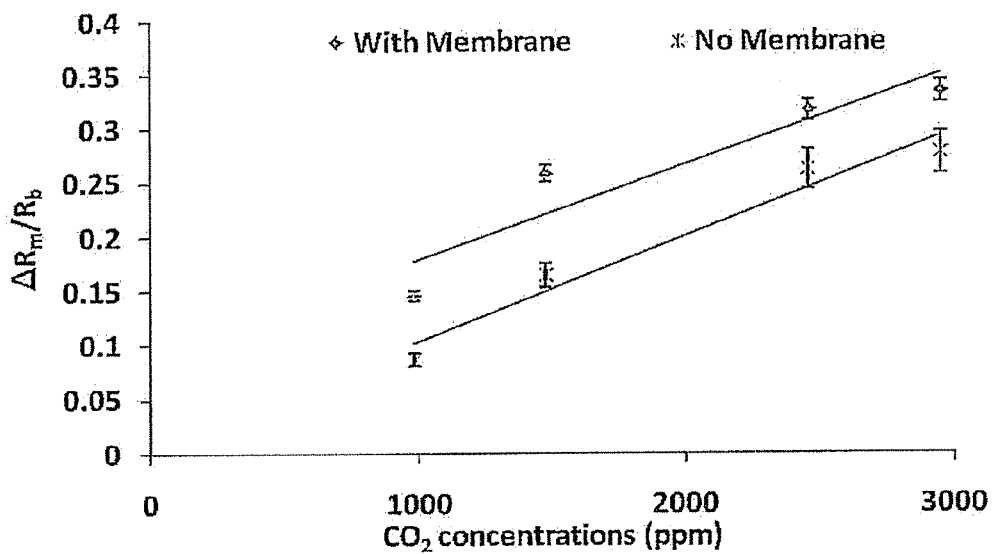
FIG. 30. Response of the PABA sensor with and without selective gas permeable PTFE membrane to various concentrations of $CO_2$ and subsequent exposure to background air at 40% RH and at 25° C.

The gas permeable membranes play an important role in limiting the diffusion rate of $CO_2$ as well as selectively pass the analyte into the electrolyte reservoir. By selecting appropriate gas permeable membranes with different pore size and thickness, the sensitivity and (or) the linear range of the sensor can be optimized to certain extent. The membranes act as a protecting cover for the electrolyte and the sensing material in the sensing reservoir on the electrode arrays. The PTFE membrane is highly selective to $CO_2$ and does not allow other gas molecules to pass through hence aiding in reducing the cross-sensitivity effect of the sensor (FIG. 30).

Effect of Cross Sensitivity

Figure 31:
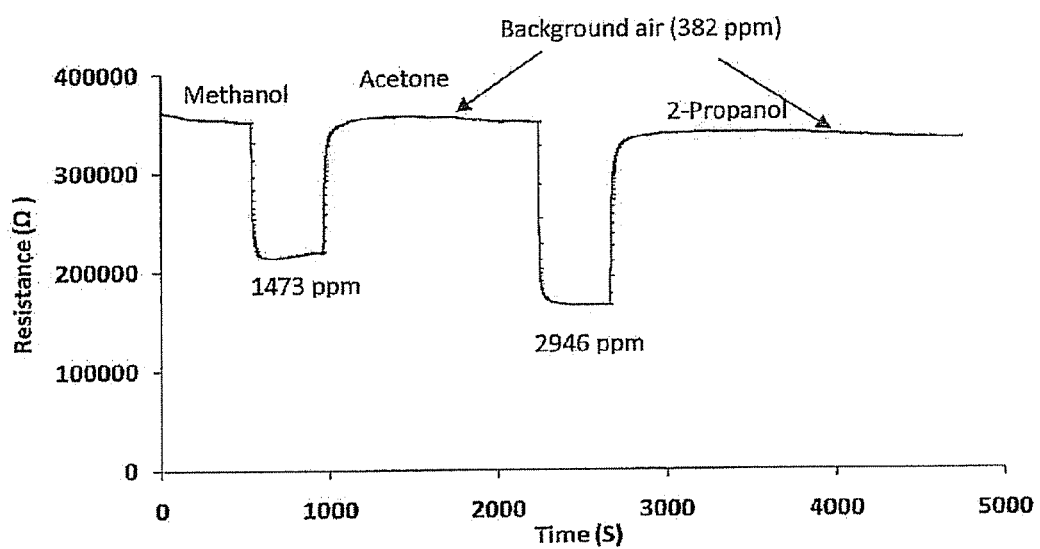
FIG. 31. Response of the PABA sensor with selective gas permeable PTFE membrane to $CO_2$, methanol, acetone and 2-propanol analytes of 1% in air at 40% RH and at 25° C.

For efficient functioning of sensors, there is a need to find out whether the sensor is interferred by other gases in addition to target analyte gas. The dc resistance values decreased with increasing $CO_2$ concentration indicating an increase of conductivity due to $CO_2$ concentration levels. But upon random exposure of 1% (percent of vapour pressure) of methanol, acetone and 1-propanol (representative of compounds expected in stored grain) in air for 3 min, followed by various levels of $CO_2$ did not change the resistivity of the sensor. The PABA-Nafion sensor works on the principle of pH change and $CO_2$ being acidic reacts with the electrolyte to induce ionic exchange resulting in decreased resistivity. The gas permeable membrane is selective to $CO_2$ and allows only $CO_2$ molecules to pass through. Hence there was no response (FIG. 31) due to alcohols and ketones in air.

Influence of PVA Electrolyte

Figure 32:
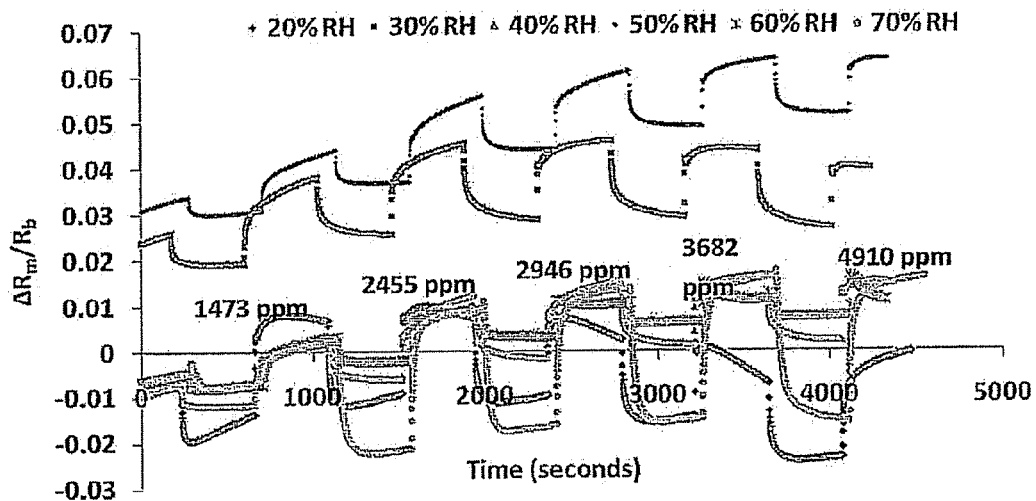
FIG. 32. Response of PABA sensor with PVA hydrogel electrolyte to various concentrations of $CO_2$ at 40% RH and at 25° C.

Similar to Nafion, Poly vinyl alcohol (PVA) is highly hydrophilic and capable of absorbing and retaining large amounts of water molecules from the atmospheric air. PABA sensors prepared with PVA electrolyte were tested under various concentrations of $CO_2$ in air. The sensor's response was similar to PABA-Nafion and a saturation curve was observed when exposed to above 2455 ppm of $CO_2$ gas (FIG. 32). As the concentration of the $CO_2$ increases, the pH changes from neutral to acidic, which causes an increase in the conductivity of proton and thereby reducing the resistance of the flowing current in the film. The PVA sensor exhibited severe drift in comparison with PABA-Nafion sensor. But PVA sensor exhibited similar reversibility characteristics in sensing the $CO_2$ analyte in comparison with PABA sensor.

Results of Experiments to Increase Sensor Detection Range

Tailoring the pH response range of PABA sensor was attempted by using KCl as a dopant. It was hypothesized that chloride anions from KCl will exchange out the phospate from PABA resulting in the dedoping of PABA and thereby inducing the ionic conductivity. This might help to increase the detection range of the sensor and hence the PABA-Nafion sensor will be able to measure above 2455 ppm levels of $CO_2$. To increase the sensor's detection range, 2 µL of PABA deposited on sensor electrodes and dried for 20 min were immersed in 20 ml of 1 M, 0.5 M, 0.1 M, 0.01 M concentrations of KCl solutions and their resistance was monitored until the resistance data stabilized. This was done to ensure that the KCl is exchanging out the phosphate. The sensor electrodes were removed from the KCl solution and dried for 30 min and a 2 µL nafion was deposited on the top of the dried PABA phosphate exchanged out material. After drying for 30 min, the electrodes were tested under different concentrations of $CO_2$ levels. The results did not show increase in the detection range and the response curves were similar with same detection window (stabilization after 2455 ppm) to the without treatment PABA-Nafion sensors.

Figure 33:
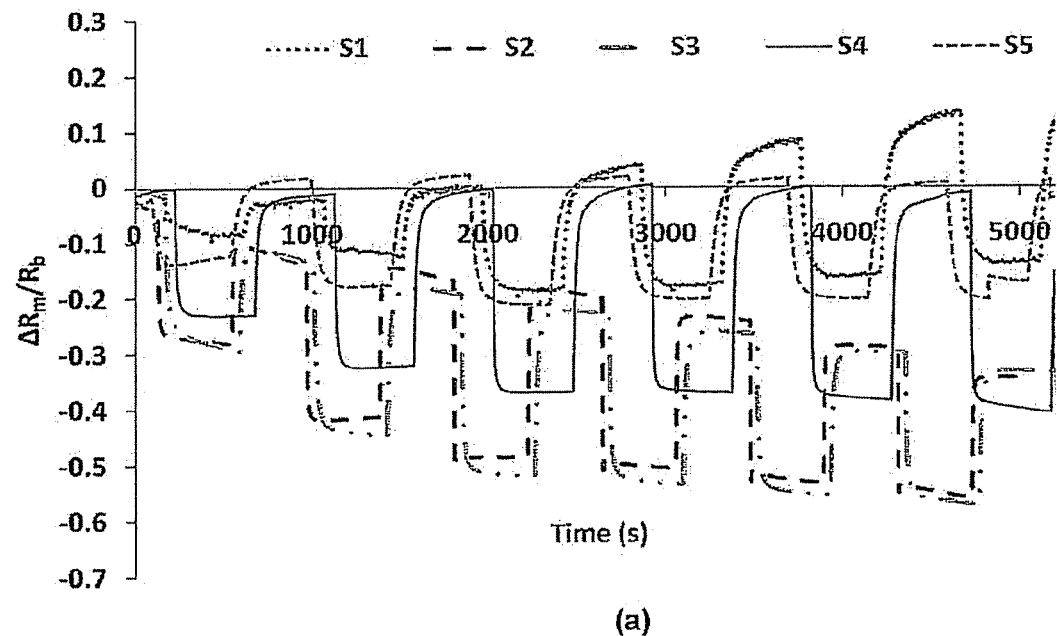
FIG. 33. Response of PABA Nafion sensor prepared with 5 different solutions to various Concentrations of $CO_2$ at 50% RH and at 25° C.
Figure 33:
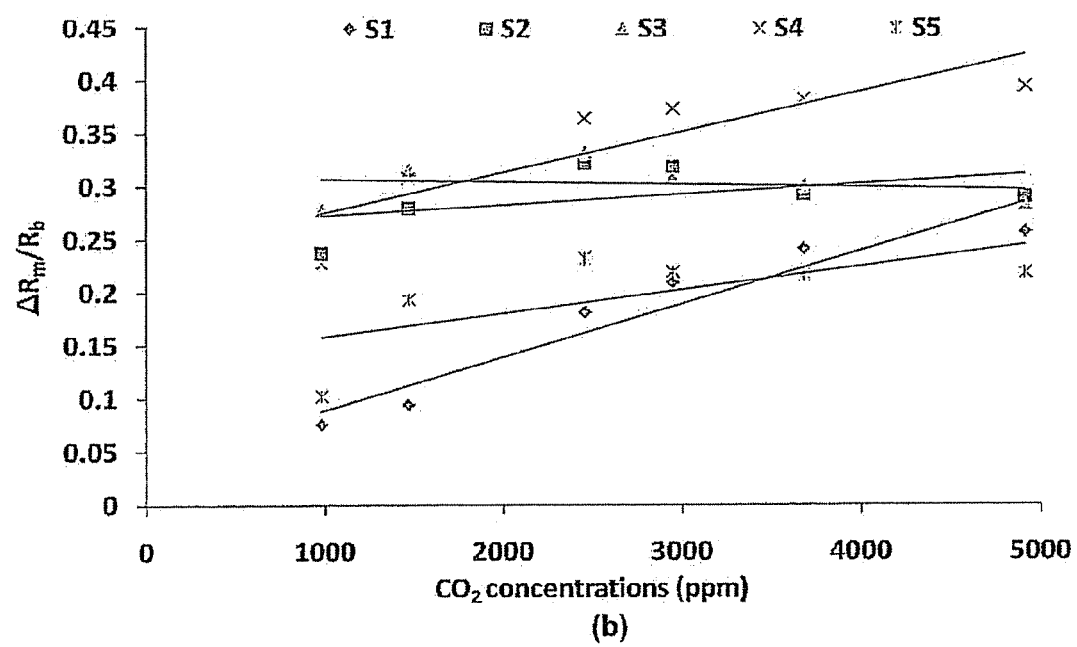

To achieve more controlled doping of KCl with phosphoric acid in PABA, five different solutions of various ratios of KCl and Phosphoric acid were prepared and PABA was dispersed in these solutions. As there are no proper methods to measure or detect the degree of exchange, the resistance values from the sensors prepared using the five different PABA solutions might give an idea of the doping levels. The resistance value of the sensors prepared from these five solutions were measured. The baseline resistance value increases due to the influence of KCl ions on PABA. Though the baseline resistance value increases (Table 4), the detection range of the sensor remains the same and the saturation effect is observed above 2455 ppm levels (FIG. 33).

The sensitivity of sensor's performance is also dependent on the surface-to-volume ratio of the polymer material.

TABLE 4

Variation in resistance due to change in ratio of $H_3PO_4$ and KCl suspension solutions used for synthesizing PABA.

| Solutions | Concentrations of Solutions Used for Suspending Synthesized PABA | Baseline Resistance in Air (Ohms)- PABA only No Nafion | Baseline Resistance in Air (Ohms)- PABA and Nafion |
|---|---|---|---|
| s1 | 0.1M $H_3PO_4$ (100 ml) | 3840 | 16,772 |
| s2 | 70 ml of 0.1M $H_3PO_4$ + 30 ml of 0.1M Kcl | 7360 | 64,108 |
| s3 | 50 ml of 0.1M Kcl + 50 ml of 0.1M $H_3PO_4$ | 5006 | 90,274 |
| s4 | 30 ml of 0.1M $H_3PO_4$ + 70 ml of 0.1M Kcl | 6385 | 304,548 |
| s5 | 100 ml of 0.1M Kcl | 8158 | 191,700 |

Sensor Packaging

Miniature sensor elements will typically not function on their own. The sensor packaging gives the sensor a suitable shape or form, provides electrical connection to the sensor, and provides a window from the sensor to the outside world. In addition, the sensor elements need mechanical and chemical protection. To package the $CO_2$ sensor for preliminary testing in bulk grain several options were considered to ensure that the packaging components avoid contamination of the sensing material and the substrate by undesirable components including grain dust and foreign material in grain. The dimensional details of the sensor chip and gas diffusion properties of the packaging material were considered in selecting the packaging components. The performance characteristics of the sensors depend on the geometry of electrodes, thermal design of the structure and the nature of the electronic interface. On practical applications, there will be a trade off between cost and performance.

Grain Bulk Measurement

Figure 35:
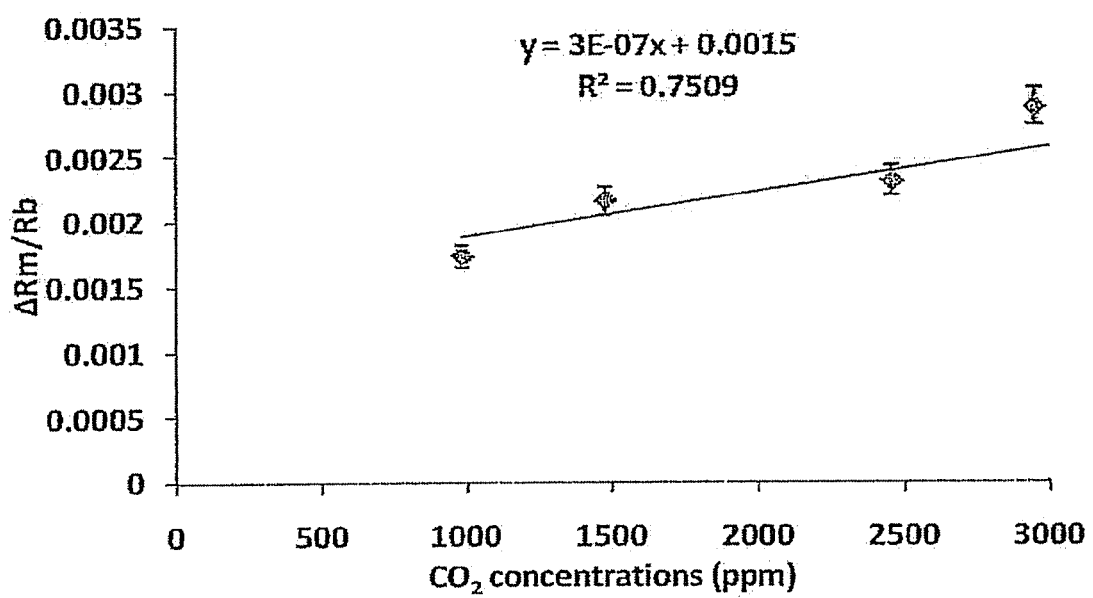
FIG. 35. Response of PABA Nafion Sensor with packaging kept inside grain bulk to concentrations of $CO_2$ at 50% RH and at 25° C.

The $CO_2$ sensor packaged in the prototype housing assembly (FIG. 34) was tested in plastic pails (4 L capacity) filled with wheat. The pails were purged with different $CO_2$ concentrations to simulate spoilage of grain. The sensor exhibited excellent response (FIG. 35) to change in $CO_2$ levels inside grain bulk. The $CO_2$ gas at desired levels was passed through the bottom of the pail while the sensor was kept immersed in the grain bulk at the top. The plastic pail was covered tightly with duct tape to prevent atmospheric exchange into the grain bulk. Gas samples from the outlet tube were analyzed using GC-MS to determine the concentrations of the outlet gas.

CONCLUSIONS

A sensitive tool for detecting incipient and or ongoing deterioration of stored grains by measuring $CO_2$ levels was developed using PABA conducting polymer. The $CO_2$ sensor can monitor the $CO_2$ concentration, which requires water in the air to operate, permitting the detection of $CO_2$ between 20 to 70% equilibrium relative humidity. The sensor dynamically detected up to 2455 ppm of $CO_2$ levels in the grain bulk. The $CO_2$ sensor exhibited dynamic performance in its response, recovery time, sensitivity, selectivity, stability and response slope. The $CO_2$ sensor responded well to various concentrations of $CO_2$ at temperatures between −25° C. to +55° C. The sensors respond to various levels of $CO_2$ at ambient temperature without artificial cooling. The packaging unit allowed measurement of $CO_2$ concentration in grain bulk. The methodology used for building the $CO_2$ sensor device is compatible with the MEMS process and can be mass manufactured using screen printing technology.

The complete disclosure of all patents, patent applications, and publications, and electronically available material cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for detecting the presence of an analyte in a fluid, comprising:
providing a sensor comprising an electrode and a polymer comprising an anilineboronic acid-phosphate complex adjacent to the electrode, wherein the sensor polymer will change an electrical characteristic in the presence of the analyte in the fluid;
exposing the sensor to a fluid containing the analyte; and
detecting a response to the exposure of the sensor to the analyte present in the fluid.

2. The method of claim 1 wherein the anilineboronic acid-phosphate complex comprises a repeating unit having the formula

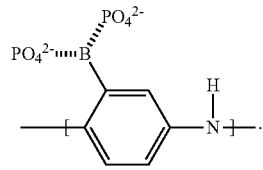

3. The method of claim 2 wherein the anilineboronic acid-phosphate complex is a copolymer, wherein the copolymer further comprises a repeating unit having a formula selected from

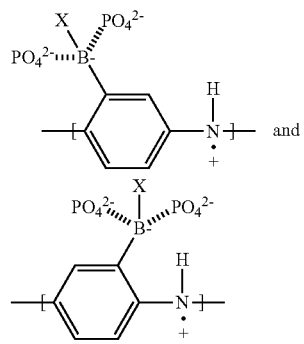

wherein X is fluoride or an amine.

4. The method of claim 3 wherein the copolymer is a random copolymer, a block copolymer, or an alternate copolymer.

5. The method of claim 1 wherein the anilineboronic acid-phosphate complex has the formula

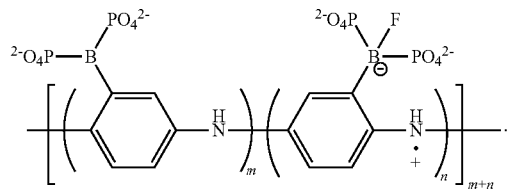

6. The method of claim 1 wherein the electrical characteristic is resistance.

7. The method of claim 1 wherein the sensor further comprises an electrolyte layer adjacent to the sensor polymer such that the sensor polymer is between the electrode and the electrolyte layer, and further comprises a selective layer adjacent to the electrolyte layer such that the electrolyte layer is between the sensor polymer and the selective layer.

8. The method of claim 1 wherein the analyte is $CO_2$ and wherein the selective layer is polytetrafluoroethylene.

9. The method of claim 1 wherein the change in the electrical characteristic in response to $CO_2$ is linear up to 2750 parts per million (ppm) $CO_2$.

10. The method of claim 1 wherein the fluid is a gas.

11. The method of claim 1 wherein the fluid is a liquid.

12. The method of claim 1 wherein the sensor is present in a body of grain or other bulk-stored commodity.

13. A system for detecting an analyte in a fluid, wherein the system comprises:
a sensor comprising an electrode and a polymer comprising an anilineboronic acid-phosphate complex adjacent to the electrode, wherein the sensor polymer will change an electrical characteristic in the presence of the analyte in the fluid; and
an analysis component configured to detect a change in the electrical characteristic of the polymer.

14. The sensor of claim 13 wherein the anilineboronic acid-phosphate complex comprises a repeating unit having the formula

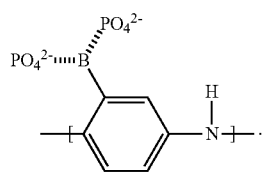

15. The sensor of claim 14 wherein the anilineboronic acid-phosphate complex is a copolymer, wherein the copolymer further comprises a repeating unit having a formula selected from

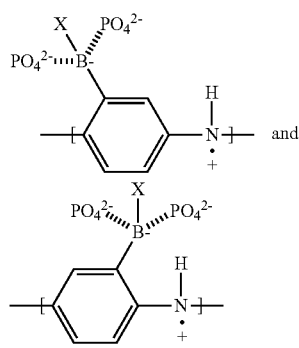

wherein X is fluoride or an amine.

16. The sensor of claim 15 wherein the copolymer is a random copolymer, a block copolymer, or an alternate copolymer.

17. The sensor of claim 13 wherein the anilineboronic acid-phosphate complex has the formula

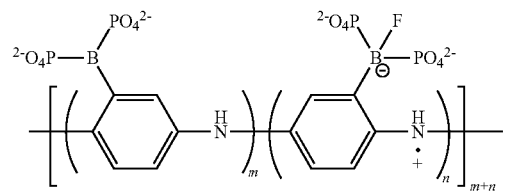

where m and n are each independently an integer greater than 2.

18. The system of claim 13 wherein the electrical characteristic is resistance.

19. The system of claim 13 wherein the sensor further comprises an electrolyte layer adjacent to the sensor polymer such that the sensor polymer is between the electrode and the electrolyte layer, and further comprises a selective layer adjacent to the electrolyte layer such that the electrolyte layer is between the sensor polymer and the selective layer.

20. The system of claim 19 wherein the analyte is $CO_2$ and wherein the selective layer is polytetrafluoroethylene.

21. The system of claim 20 wherein the change in the electrical characteristic in response to $CO_2$ is linear up to 2750 parts per million (ppm) $CO_2$.

22. The system of claim 13 wherein the fluid is a gas.

23. The system of claim 13 wherein the fluid is a liquid.

24. A sensor comprising:
an electrode; and
a sensor polymer comprising a polymer comprising an anilineboronic acid-phosphate complex adjacent to the electrode.

25. The sensor of claim 24 wherein the anilineboronic acid-phosphate complex comprises a repeating unit having the formula

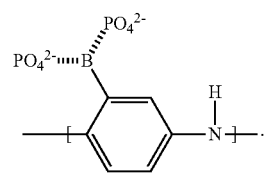

26. The sensor of claim 25 wherein the anilineboronic acid-phosphate complex is a copolymer, wherein the copolymer further comprises a repeating unit having a formula selected from

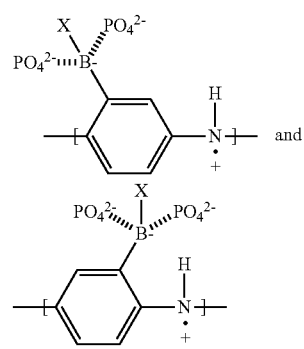

wherein X is fluoride or an amine.

27. The sensor of claim 26 wherein the copolymer is a random copolymer, a block copolymer, or an alternate copolymer.

28. The sensor of claim 24 wherein the anilineboronic acid-phosphate complex has the formula

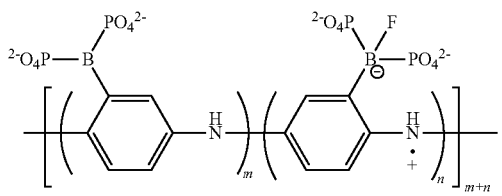

where m and n are each independently an integer greater than 2.

29. The sensor of claim 24 wherein the sensor further comprises an electrolyte layer adjacent to the sensor polymer such that the sensor polymer is between the electrode and the electrolyte layer.

30. The sensor of claim 29 wherein the electrolyte layer is electrically coupled to the sensor polymer.

31. The sensor of claim 29 wherein the electrolyte layer comprises a sulfonated tetrafluoroethylene based fluoropolymer-copolymer, poly(vinyl alcohol), or ionic liquid.

32. The sensor of claim 24 wherein the sensor further comprises a selective layer adjacent to the sensor polymer such that the sensor polymer is between the electrode and the selective layer.

33. The sensor of claim 32 wherein the sensor further comprises an electrolyte layer adjacent to the sensor polymer such that the electrolyte layer is between the sensor polymer and the selective layer.

34. The sensor of claim 24 wherein the sensor further comprises an analysis component electrically coupled to the electrode.

* * * * *